United States Patent
Nakashima et al.

(10) Patent No.: US 7,745,537 B2
(45) Date of Patent: Jun. 29, 2010

(54) PARTICULATE WATER ABSORBING AGENT, WATER-ABSORBENT CORE AND ABSORBING ARTICLE

(75) Inventors: Yasuhisa Nakashima, Hyogo (JP); Toshihiro Takaai, Hyogo (JP); Katsuyuki Wada, Hyogo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 11/817,839

(22) PCT Filed: Apr. 6, 2006

(86) PCT No.: PCT/JP2006/307795

§ 371 (c)(1), (2), (4) Date: Sep. 5, 2007

(87) PCT Pub. No.: WO2006/109844

PCT Pub. Date: Oct. 19, 2006

(65) Prior Publication Data

US 2009/0008604 A1    Jan. 8, 2009

(30) Foreign Application Priority Data

Apr. 6, 2005  (JP) .............................. 2005-109779

(51) Int. Cl.
 C08L 33/02 (2006.01)
(52) U.S. Cl. ................. 525/119; 525/329.5; 525/329.7; 525/384; 428/402; 252/194
(58) Field of Classification Search ................. 252/194; 525/119, 329.5, 329.7, 384; 428/402; 524/556, 524/9; 526/77, 317.1, 318.5, 319
See application file for complete search history.

(56) References Cited

U.S. PATENT DOCUMENTS

| | | |
|---|---|---|
| 4,093,776 A | 6/1978 | Aoki et al. |
| 4,286,082 A | 8/1981 | Tsubakimoto et al. |
| 4,367,323 A | 1/1983 | Kitamura et al. |
| 4,446,261 A | 5/1984 | Yamasaki et al. |
| 4,625,001 A | 11/1986 | Tsubakimoto et al. |
| 4,683,274 A | 7/1987 | Nakamura et al. |
| RE32,649 E | 4/1988 | Brandt et al. |
| 4,755,562 A | 7/1988 | Alexander et al. |
| 4,824,901 A | 4/1989 | Alexander et al. |
| 4,873,299 A | 10/1989 | Nowakowsky et al. |
| 4,973,632 A | 11/1990 | Nagasuna et al. |
| 4,985,518 A | 1/1991 | Alexander et al. |
| 5,124,416 A | 6/1992 | Haruna et al. |
| 5,140,076 A | 8/1992 | Hatsuda et al. |
| 5,145,906 A | 9/1992 | Chambers et al. |
| 5,244,735 A | 9/1993 | Kimura et al. |
| 5,250,640 A | 10/1993 | Irie et al. |
| 5,264,495 A | 11/1993 | Irie et al. |
| 5,380,808 A | 1/1995 | Sumiya et al. |
| 5,409,771 A | 4/1995 | Dahmen et al. |
| 5,744,564 A | 4/1998 | Stanley, Jr. et al. |
| 6,043,311 A | 3/2000 | Houben et al. |
| 6,071,976 A | 6/2000 | Dairoku et al. |
| 6,110,992 A | 8/2000 | Wada et al. |
| 6,228,930 B1 | 5/2001 | Dairoku et al. |
| 6,254,990 B1 | 7/2001 | Ishizaki et al. |
| 6,265,488 B1 | 7/2001 | Fujino et al. |
| 6,323,252 B1 | 11/2001 | Gartner et al. |
| 6,335,406 B1 | 1/2002 | Nagasuna et al. |
| 6,414,214 B1 | 7/2002 | Engelhardt et al. |
| 6,469,080 B2 | 10/2002 | Miyake et al. |
| 6,472,478 B1 | 10/2002 | Funk et al. |
| 6,503,978 B1 | 1/2003 | Tsao et al. |
| 6,605,673 B1 | 8/2003 | Mertens et al. |
| 6,620,889 B1 | 9/2003 | Mertens et al. |
| 7,312,278 B2 * | 12/2007 | Nakashima et al. .......... 525/119 |
| 2004/0048955 A1 * | 3/2004 | Wada et al. .................... 524/9 |
| 2004/0071966 A1 | 4/2004 | Inger et al. |
| 2005/0020780 A1 | 1/2005 | Inger et al. |

FOREIGN PATENT DOCUMENTS

| | | |
|---|---|---|
| CA | 2433044 | 7/2002 |
| CN | 1059153 | 3/1992 |
| EP | 0811636 | 12/1997 |
| EP | 0955086 | 11/1999 |
| EP | 1352927 | 10/2003 |
| EP | 1419755 | 5/2004 |
| EP | 1516884 | 3/2005 |
| EP | 0922717 | 9/2007 |
| JP | 9124879 | 5/1997 |
| JP | 2002539281 | 11/2002 |
| JP | 200418565 | 1/2004 |
| JP | 2004517173 | 6/2004 |
| WO | 9305080 | 3/1993 |
| WO | 9505856 | 3/1995 |

(Continued)

OTHER PUBLICATIONS

The Rising Materials of Sanitary—Napkins and Paper Diapers, 1994, and partial English translation of col. 3 of document.

*Primary Examiner*—Harold Y Pyon
*Assistant Examiner*—Bijan Ahvazi
(74) *Attorney, Agent, or Firm*—Roylance, Abrams, Berdo & Goodman, L.L.P.

(57) ABSTRACT

The present invention provides a particulate water absorbing agent for absorbent cores which is excellent in powder conveying property, and achieves sufficient absorption performances for use in absorbent cores in particulate water absorbing agents including a water absorbing resin as a principal component, and which further is suitable for practical applications. In the present invention, characteristics that had not been known conventionally at all, i.e., "permeability potential under pressure (PPUP)" and "frictional charge being a positive charge" of the particulate water absorbing agent are regulated at a time, and furthermore, regulation of the "moisture content of 2 to 10% by weight" is perfected. Also, the particulate water absorbing agent including (A) a water-swelling crosslinked polymer having a constitutional unit derived from an unsaturated monomer containing an acid group and/or a salt thereof; and (B) water fulfills certain requirements.

7 Claims, No Drawings

FOREIGN PATENT DOCUMENTS

| WO | WO02/100451 A2 * | 12/2002 |
| WO | 03104349 | 5/2003 |
| WO | 2004069404 | 8/2004 |
| WO | 2004069915 | 8/2004 |
| WO | 2004069936 | 8/2004 |
| WO | 2005010102 | 2/2005 |

* cited by examiner

PARTICULATE WATER ABSORBING AGENT, WATER-ABSORBENT CORE AND ABSORBING ARTICLE

TECHNICAL FIELD

The present invention relates to a particulate water absorbing agent including a water absorbing resin (also referred to as water-swelling crosslinked polymer) as a principal component, a water-absorbent core and an absorbing article in which this particulate water absorbing agent is used. More particularly, the present invention relates to a particulate water absorbing agent for absorbent cores which may be used in disposable diapers, sanitary napkins and the like, the particulate water absorbing agent being excellent in the powder conveying property, and having excellent absorption ability not found in conventional products.

BACKGROUND ART

At present, in sanitary goods such as a disposable diaper, a sanitary napkin, a so-called incontinence pad and the like, a water absorbing resin (particulate water absorbing agent) and a hydrophilic fiber such as pulp aiming at absorption of body fluids have been widely employed as their component material.

Conventionally, known water-absorption properties expected for the water absorbing resin as described above involve many characteristics (parameters) such as centrifuge retention capacity, absorbency against pressure, water-absorption speed, liquid permeability without pressure, liquid permeability under pressure, impact resistance, resistance to urine, flowability, gel strength, color, particle size and the like. In addition, with regard to the same physical property (e.g., centrifuge retention capacity), many definitions according to various aspects (parameter measurement methods) were proposed.

For example, Document 1 proposes a water absorbing resin that is excellent in liquid permeability and impact resistance. Documents 2 to 4 propose a water absorbing resin subjected to surface crosslinking in which an aqueous cation solution is used. Document 5 proposes a water absorbing resin and the like in which the moisture content was regulated for ameliorating fragility of the particles. Furthermore, Document 6 proposes a water absorbing resin having a certain moisture content and having a certain absorbency against pressure. Additionally, Document 7 proposes a hydrogel subjected to coating with a steric or electrostatic spacer.

The water absorbing resins (particulate water absorbing agents) which have been developed while focusing on these many physical properties have been produced and used through targeting these physical properties, or as products having such physical properties. However, even though the aforementioned numerous physical properties (e.g., "centrifuge retention capacity", "absorbency against pressure" and the like) were regulated, powder conveying property was inferior. Furthermore, there still exists a problem of hardly achieving sufficient performance in practical applications in absorbent cores such as disposable diapers and the like.

[Document 1] U.S. Pat. No. 6,414,214
[Document 2] U.S. Pat. No. 6,620,889
[Document 3] JP-T-2002-539281
[Document 4] JP-T-2003-529647
[Document 5] JP-A-H9-124879
[Document 6] U.S. Pat. No. 6,323,252
[Document 7] JP-T-2004-517173
("JP-T": Japanese translation of PCT international application)

DISCLOSURE OF THE INVENTION

Problem to be solved by the present invention is to provide a particulate water absorbing agent for use in an absorbent core, which is excellent in powder conveying property, can achieve sufficient absorption performance for use in absorbent cores, and further, is suitable for practical applications.

Under the circumstances in which numerous water absorbing resins (particulate water absorbing agents) having regulated parameter physical properties have been proposed, the present inventor newly focused on characteristics of "permeability potential under pressure (PPUP)" and "frictional charge" of the water absorbing resin from completely novel perspectives. Moreover, it was found that these two novel characteristics and "moisture content" are important factors in practical applications of water absorbing resins.

In other words, the present inventor found that a particulate water absorbing agent in which conventionally known "centrifuge retention capacity" and "absorbency against pressure", as well as "permeability potential under pressure (PPUP)" and "frictional charge" which are characteristics that had not been conventionally known at all are regulated to fall within a certain range, and in addition to the above four characteristics, "moisture content" is additionally regulated to fall within a certain range will be a water absorbing resin (particulate water absorbing agent) which can be optimally used in absorbent cores in practical applications. Accordingly, the present invention was accomplished.

Hence, the particulate water absorbing agent of the present invention comprises: (A) a water-swelling crosslinked polymer having a constitutional unit derived from an unsaturated monomer containing an acid group and/or a salt thereof; and (B) water, said particulate water absorbing agent having:

(a) centrifuge retention capacity (CRC) for a 0.90% by weight aqueous sodium chloride solution being 28 to 50 g/g;

(b) absorbency against pressure (AAP: 0.90 g) being 20 to 40 g/g;

(c) moisture content determined on the basis of the weight loss in drying at 105° C. for 3 hrs being 2 to 10% by weight;

(d) positive frictional charge when the moisture content determined on the basis of the weight loss in drying at 105° C. for 3 hrs is not higher than 0.5% by weight; and (e) permeability potential under pressure (PPUP) being 60 to 100% specified by the following formula (I):

$$PPUP(\%) = (AAP: 5.0\ g)/(AAP: 0.90\ g) * 100 \quad (I)$$

wherein (AAP: 0.90 g) is the absorbency against pressure measured with 0.90 g of the particulate water absorbing agent for a 0.90% by weight aqueous sodium chloride solution under a pressure (load) of 4.8 kPa for 60 min; and (AAP: 5.0 g) is the absorbency against pressure measured with 5.0 g of the particulate water absorbing agent for a 0.90% by weight aqueous sodium chloride solution under a pressure (load) of 4.8 kPa for 60 min.

According to the particulate water absorbing agent of the present invention, excellent absorption ability which had not been found conventionally may be achieved in practical applications such as diapers.

BEST MODE FOR CARRYING OUT THE INVENTION

Hereinafter, materials, conditions for reaction and the like employed for the water absorbing resin and the particulate water absorbing agent of the present invention will be explained.

(1) Water Absorbing Resin (May be Also Referred to as Water-Swelling Crosslinked Polymer)

The water absorbing resin of the present invention means a crosslinked polymer which can form a hydrogel, and has a water-swelling property and water insolubility. The water-swelling property means the property to have a centrifuge retention capacity (CRC) in ion exchanged water of not less than 5 g/g, and preferably 50 to 1000 g/g, i.e., one that absorbs large quantity of water. Also, the water insolubility means that proportion of water extractables (specified with equilibrium extractable polymer in U.S. Reissue Pat. No. Re 32649) is essentially 0 to 50% by weight, preferably 0 to 25% by weight, and more preferably 0 to 15% by weight.

Preferable water absorbing resin according to the present invention (may be also referred to as water-swelling crosslinked polymer) has a constitutional unit derived from an acid group and/or a salt thereof. Preferable water absorbing resin according to the present invention may be a polymer prepared by subjecting an unsaturated monomer containing an acid group and/or a salt thereof to crosslinking polymerization in the range to have a water-swelling property. Particularly preferably, a polyacrylic partially neutralized polymer obtained by allowing an unsaturated monomer including acryl acid and/or a salt thereof (neutralized product) as a principal component to be polymerized and crosslinked may be used as the water absorbing resin according to the present invention (may be also referred to as water-swelling crosslinked polymer). This polyacrylic partially neutralized polymer has a constitutional unit derived from acrylic acid and/or a salt thereof.

In the present invention, the "water absorbing resin" means a polymer crosslinked its inside alone, and/or a polymer crosslinked the inside and on the surface thereof. Particularly, the "water absorbing resin subjected to a surface treatment" means a polymer crosslinked inside and on the surface thereof.

(2) Particulate Water Absorbing Agent and Method for Production of the Same

In the present invention, the particulate water absorbing agent is an absorption and fixation agent which includes a water absorbing resin as a principal component, and which can go solid an aqueous liquid through absorbing an aqueous liquid. Moreover, this particulate water absorbing agent essentially contains a certain amount of water (moisture content of 2 to 10% by weight). The content of the water absorbing resin is preferably 70 to 98% by weight, more preferably 80 to 98% by weight; and more preferably 90 to 98% by weight of the total. Additionally, the additive described later may be used as needed. The aqueous liquid is not particularly limited to water as long as it includes water such as urine, blood, feces, waste liquid, moisture and vapor, ice, mixture of water and an organic solvent or an inorganic solvent, rainwater and groundwater. Preferably, the aqueous liquid is urine, and more preferably human urine. The particulate water absorbing agent of the present invention may be preferably, an absorption and fixation agent for human urine. In the present invention, the particle shape is not particularly limited. Illustrative examples of the particle shape include spherical shape, suborbicular shape, elliptical shape, irregularly pulverized shape, rod-like shape, polyhedron-like shape, sausage-like shape (illustrated in U.S. Pat. No. 4,973,632) and creased shape (illustrated in U.S. Pat. No. 5,744,564). The particle may be a single particle, a agglomerate particle or mixture thereof. The particle may be a foamed porous. The single particle or the agglomerate particle of irregularly pulverized shape illustrated preferably as the particle.

In the method for the production of a particulate water absorbing agent of the present invention, for example, the particulate water absorbing agent may be obtained by subjecting a water absorbing resin having a certain particle size and a certain centrifuge retention capacity described later to surface crosslinking with a particular surface crosslinking agent described later, thereby elevating the "absorbency against pressure (AAP: 0.9 g)" to not less than 20 g/g while keeping the "centrifuge retention capacity (CRC)" falling within the range of the present invention being 28 to 50 g/g, and then, adding thereto water to give the certain "moisture content" described later.

Such a particulate water absorbing agent of the present invention may be obtained by, for example, using a water absorbing resin having a centrifuge retention capacity (CRC) for a physiological saline solution of not less than 28 g/g through lowering the absorption capacity (CRC) of this water absorbing resin to 95 to 50% of the absorption capacity (CRC) before the surface crosslinking by way of surface crosslinking of a particular surface crosslinking agent, followed by further regulating the moisture content. As the aforementioned water absorbing resin having a centrifuge retention capacity (CRC) for a physiological saline solution of not less than 28 g/g, for example, a water absorbing resin having: a weight average particle diameter being 200 to 500 μm; ratio of particles of smaller than 150 μm being 0 to 8% by weight; bulk density (specified by JIS K-3362) being 0.40 to 0.90 g/ml; particles in between 600 to 150 μm accounting for 60 to 100% by weight of the total; and logarithmic standard deviation (σζ) of the particle size distribution being 0.20 to 0.50 may be used. In the present specification, the terms "weight average particle diameter" are synonymous with the terms "mass average particle diameter". In the present specification, the terms "part by weight" and "% by weight" are synonymous with the terms "part by mass" and "% by mass", respectively.

(3) Permeability Potential Under Pressure (PPUP)

One aspect of the present invention is that "permeability potential under pressure (PPUP)" that had not been known conventionally at all was specified. This "permeability potential under pressure (PPUP)" may fall within the range specified according to the present invention through subjecting a water absorbing resin having the certain particle size and the certain centrifuge retention capacity to surface crosslinking with the particular surface crosslinking agent described later.

The permeability potential under pressure (PPUP) newly found according to the present invention is specified by the following formula (I):

$$\text{PPUP}(\%) = (\text{AAP: } 5.0 \text{ g})/(\text{AAP: } 0.90 \text{ g}) * 100 \quad (I)$$

wherein, (AAP: 0.90 g) is an absorbency against pressure under a pressure of 4.8 kPa for a 0.90% by weight aqueous sodium chloride solution for 60 min, as measured with 0.90 g of the particulate water absorbing agent. Furthermore, (AAP: 5.0 g) is an absorbency against pressure under a pressure of 4.8 kPa for a 0.90% by weight aqueous sodium chloride solution for 60 min, as measured with 5.0 g of the particulate water absorbing agent.

Importance of the absorbency against pressure (AAP: 0.9 g) has been known so far, and a number of absorbencies against pressure have been specified with varying measurement time (for example, 5 min to 3 hrs), liquid to be absorbed (for example, various artificial urine, physiological saline solution, ion exchanged water, aqueous L-ascorbic acid solution), load (for example, 0.01 psi to 1.4 psi), measurement particle size in measurement (for example, total particle size/ or cut from 600 to 300 μm) and the like. However, unlike such conventional absorbencies against pressure, the permeability potential under pressure (PPUP) according to the present invention is an entirely new marker in connection with the stability of the absorbency against pressure (AAP) when the amount of the water absorbing resin or the particulate water absorbing agent (amount per unit area of the measurement) is increased from 0.90 g to 5.0 g. In other words, the permeability potential under pressure (PPUP) of the present invention is an entirely new marker in connection with less lowering of the absorbency against pressure (AAP) when the amount of the water absorbing resin or the particulate water absorbing agent (amount per unit area of the measurement) is increased from 0.90 g to 5.0 g. The permeability potential under pressure (PPUP) of the present invention is a novel parameter newly specified according to the spirit of the present invention.

In spite of high absorbency against pressure (AAP) of conventional water absorbing resins as measured by various measurement methods which had been conventionally proposed, their performance could not be achieved in diapers in practical applications. As a result of elaborate investigation of the grounds therefor, the present inventor found that the absorbency against pressure (AAP) may vary depending on the amount of the water absorbing resin or the particulate water absorbing agent per unit area even under the same load (compression). Still further, the present inventor found that the amount of the water absorbing resin or the particulate water absorbing agent (amount per unit area of the measurement) may partially vary in the diaper, and that the variation of the absorbency against pressure (AAP) resulting from alteration of the resin amount may be the grounds for deterioration of the physical properties of the diaper in practical applications. Accordingly, the present invention was accomplished.

The particulate water absorbing agent of the present invention has very high (PPUP) specified by the following formula (I), and stably achieves high physical properties in any amount of the water absorbing resin (any amount of the particulate water absorbing agent) in the diaper (concentration). Further, high liquid permeability may be also achieved.

PPUP(%)=(AAP: 5.0 g)/(AAP: 0.90 g)*100     (I)

(4) Positive Frictional Charge

In addition to the aforementioned permeability potential under pressure (PPUP), a property of the water absorbing agent newly specified by the present invention is "positive (plus) frictional charge". Moreover, the "positive (plus) frictional charge" may be regulated by combination of a particular water absorbing resin and a particular surface crosslinking agent.

The particulate water absorbing agent having such a "positive (plus) frictional charge" is accompanied by comparatively uniform surface crosslinkage, therefore, it exhibits high superior properties as a particulate water absorbing agent, and in addition, it exhibits a superior physical properties also in practical applications as a diaper. The particulate water absorbing agent having a "positive (plus) frictional charge" exhibits comparatively uniform surface crosslinkage. Additionally, the absorbent core formed with the particulate water absorbing agent having a "positive (plus) frictional charge" and pulp (having a "negative (minus) frictional charge" according to the measurement method described later) provides excellent diapers. By allowing the frictional charge of the particulate water absorbing agent to be a positive charge, uniform mixing performance of the particulate water absorbing agent with the pulp may be also improved. Moreover, the particulate water absorbing agent having a "positive (plus) frictional charge" exhibits an excellent powder conveying property through regulating the certain moisture content described later.

(5) Unsaturated Monomer

The water absorbing resin which may have a plus "frictional charge" through the combination with the particular surface crosslinking agent described later is preferably a water absorbing resin in which acryl acid and/or a monovalent salt thereof is used as a principal component. A monomer other than acryl acid (salt) may be used in combination in the range to give the plus "frictional charge", or the water absorbing resin may be obtained solely from the monomer other than acryl acid (salt).

When the monomer other than acryl acid (salt) is used in the present invention, ratio of the monomer other than acryl acid (salt) may be preferably 0 to 30% by mole, more preferably 0 to 10% by mole, and most preferably 0 to 5% by mole of total amount of acryl acid and a salt thereof used as a principal component for achieving the advantage of the present invention.

In addition, when an unsaturated monomer including an acid group is used as a monomer, examples of the preferred salt include alkali metal salts, alkali earth metal salts, ammonium salts and the like. In view of the performance, industrial availability, safety and the like of the resulting water absorbing resin, sodium salts or potassium salts are preferred.

Moreover, in light of the aspects of the physical property and pH, the unsaturated monomer containing an acid group such as acryl acid preferably has a neutralized acid group. The neutralization ratio of the acid group is usually 20 to 100% by mole, more preferably 30 to 95% by mole, and more preferably 40 to 80% by mole. Neutralization of the acid group may be conducted on a monomer or on a polymer, both of which may be conducted in combination.

(6) Crosslinkable Monomer (Internal Crosslinking Agent)

The water absorbing resin of the present invention is a crosslinked polymer, and the procedure for the crosslinking is not limited. This crosslinked polymer may be the self-crosslinked type in which any crosslinkable monomer is not used. In this regard, this crosslinked polymer may be preferably obtained by allowing a crosslinkable monomer having 2 or more polymerizable unsaturated groups, 2 or more reactive groups in one molecule (may be also referred to as internal crosslinking agent of the water absorbing resin) to be copolymerized or reacted, in light of the physical property. In addition, the water absorbing resin of the present invention being a crosslinked polymer may be also specified by being non-dissolving in water as described above.

Specific examples of the internal crosslinking agent include e.g., N,N'-methylenebis(meth)acrylamide, (poly)ethylene glycol di(meth)acrylate, (poly)propylene glycol di(meth)acrylate, trimethylolpropane tri(meth)acrylate, glycerine tri(meth)acrylate, glycerine acrylate methacrylate, ethylene oxide modified trimethylolpropane tri(meth)acrylate, pentaerythritol hexa(meth)acrylate, triallyl cyanurate, triallyl isocyanurate, triallyl phosphate, triallylamine, poly(meth)allyloxyalkane, (poly)ethylene glycol diglycidyl ether, glycerol diglycidyl ether, (poly)ethylene glycol, propylene glycol, glycerine, pentaerythritol, ethylenediamine, ethylene carbonate, propylene carbonate, polyethyleneimine, glycidyl (meth)acrylate, and the like.

These internal crosslinking agents may be used alone, or as a mixture of two or more kinds ad libitum. Also, these internal crosslinking agents may be added as a whole into the reaction system or in portion wise. Furthermore, the internal crosslinking agent may be added to the reaction system before, during or after the polymerization of the monomer, or after the neutralization.

In order to obtain the particulate water absorbing agent of the present invention, using amount of these internal crosslinking agents is preferably in the range of 0.001 to 2% by mole, more preferably 0.005 to 0.5% by mole, further preferably 0.01 to 0.2% by mole, and particularly preferably 0.03 to 0.15% by mole based on the aforementioned monomer (excluding the internal crosslinking agents). In order to obtain the water absorbing agent of the present invention, it is preferred that a compound having 2 or more polymerizable unsaturated groups is essentially used in polymerization as an internal crosslinking agent.

(7) Polymerization Initiator

Examples of polymerization initiator which may be used in polymerization of the monomer to obtain the water absorbing resin used in the present invention include radical polymerization initiators such as potassium persulfate, ammonium persulfate, sodium persulfate, potassium peracetate, sodium peracetate, potassium percarbonate, sodium percarbonate, tert-butyl hydroperoxide, hydrogen peroxide and 2,2'-azobis (2-amidinopropane)dihydrochloride; and photopolymerization initiators such as 2-hydroxy-2-methyl-1-phenylpropane-1-one. In order to obtain the water absorbing agent of the present invention, using amount of the polymerization initiator is preferably 0.001 to 2% by mole, and more preferably 0.01 to 0.1% by mole (based on total monomers).

(8) Polymerization Method and Polymerization Solution

Although bulk polymerization or precipitation polymerization can be carried out in the present invention, it is preferred in light of the physical properties that aqueous polymerization or reversed phase suspension polymerization is carried out using the aforementioned monomer in an aqueous solution.

When the monomer is prepared to give an aqueous solution, concentration of the monomer in the aqueous solution (hereinafter, referred to as aqueous monomer solution) is not particularly limited but may be determined depending on the temperature or the monomer of the aqueous solution. The concentration may be preferably 10 to 70% by weight, and more preferably 20 to 60% by weight. Additionally, when the aforementioned aqueous polymerization is carried out, a solvent other than water may be used in combination as needed. In this instance, type of the solvent which may be used in combination is not particularly limited. The polymer obtained by polymerization may be pulverized as needed.

Upon allowing for initiation of the aforementioned polymerization, the polymerization initiator as described above is used to permit the initiation. Also, in addition to the aforementioned polymerization initiator, active energy ray such as ultraviolet ray, electron ray or γ-ray may be used alone, or in combination with the polymerization initiator. Temperature upon initiation of the polymerization may vary depending on the used polymerization initiator, but falls preferably within the range of 15 to 130° C., and more preferably within the range of 20 to 120° C.

The reversed phase suspension polymerization means a polymerization process in which an aqueous monomer solution is suspended in a hydrophobic organic solvent, and is described in, for example, U.S. Pat. Nos. 4,093,776, 4,367,323, 4,446,261, 4,683,274, 5,244,735 and the like. The aqueous polymerization means a process for allowing an aqueous monomer solution to be polymerized without using a dispersion solvent, and is described in, for example, U.S. Pat. Nos. 4,625,001, 4,873,299, 4,286,082, 4,973,632, 4,985,518, 5,124,416, 5,250,640, 5,264,495, 5,145,906, 5,380,808 and the like, as well as European Patent Nos. 0811636, 0955086, 0922717 and the like. The monomer, initiator and the like illustrated in these polymerization processes can be also applied in the present invention.

(9) Addition of Chain Transfer Agent

In the method for production of the present invention, a chain transfer agent may be used in polymerization. When the water absorbing resin obtained by polymerization in the presence of an aqueous chain transfer agent in addition to the aforementioned unsaturated monomer, internal crosslinking agent and polymerization initiator is used as the particulate water absorbing agent of the present invention, an absorbent core with high absorbing ability and superior stability against urine can be obtained. Examples of the chain transfer agent which can be used are illustrated in, for example, U.S. Pat. Nos. 6,335,406, 6,110,992, 6,043,311 and the like.

Using amount of the aqueous chain transfer agent depends on kind of the aqueous chain transfer agent and concentration of the aqueous monomer solution, but may be 0.001 to 1% by mole, and preferably 0.005 to 0.3% by mole based on the total monomers.

(10) Drying

The aforementioned crosslinked polymer is in the form of hydrogel crosslinked polymer, and the crosslinked polymer may be pulverized in the state of the gel as needed, followed by further drying. The drying may be carried out in the temperature range (specified as the heating medium temperature) of usually 60° C. to 250° C., preferably 100° C. to 220° C., and more preferably 120° C. to 200° C. Drying time period depends on the surface area of the polymer, moisture content and type of the dryer, and may be determined to give the intended moisture content.

Moisture content of the water absorbing resin which may be used in the present invention (specified in Examples) is not particularly limited, but particles (powder) that exhibit the flowability even at a room temperature are preferred for obtaining the particulate water absorbing agent of the present invention. For attaining the particulate water absorbing agent of the present invention, this water absorbing resin has a moisture content of preferably 0.2 to 30% by weight, more preferably 0.3 to 15% by weight, and particularly preferably 0.5 to 10% by weight.

Examples of the drying method which may be employed include drying by heating, hot-air drying, drying under reduced pressure, infra-red drying, microwave drying, dehydration by azeotropy with a hydrophobic organic solvent, high humidity drying using water vapor at a high temperature and the like. Any of a variety of drying methods may be employed so that intended moisture content can be provided. This drying method is not particularly limited.

(11) Pulverization, Classification and Particle Size Control, and Absorption Capacity The water absorbing resin (cross-linked polymer) of the present invention is adjusted preferably to have specific particle size as powder for attaining the particulate water absorbing agent of the present invention.

In connection with the particle size of the water absorbing resin (crosslinked polymer particle) of the present invention, it is preferred that the weight average particle diameter is regulated to fall within a narrow range of usually 200 to 500 μm, preferably 230 to 480 μm, more preferably 250 to 450 μm, and particularly preferably 280 to 450 μm for attaining the particulate water absorbing agent of the present invention. In addition, the water absorbing resin of the present invention is further regulated to have a ratio of particles smaller than 150 μm being 0 to 8% by weight, preferably 0 to 5% by weight, and more preferably 0 to 3% by weight.

Furthermore, the water absorbing resin of the present invention is adjusted to have a bulk density (specified by JIS K-3362) falling within the range of preferably 0.40 to 0.90 g/ml, and more preferably 0.50 to 0.80 g/ml in order to attain the particulate water absorbing agent of the present invention. Additionally, in the water absorbing resin of the present invention, particles in between 600 to 150 μm may account for preferably 60 to 100% by weight, more preferably 70 to 100% by weight, and still more preferably 80 to 100% by weight of the total. The water absorbing resin of the present invention has a logarithmic standard deviation (σζ) of the particle size distribution of preferably 0.20 to 0.50, more preferably 0.20 to 0.45, and particularly preferably 0.20 to 0.40.

Adjustment of the particle size may be perfected by dispersion polymerization and dispersion drying in the particulate form as in reversed phase suspension polymerization. Generally, in case of the aqueous polymerization in particular, pulverization and classification may be conducted after drying to adjust to give a certain particle size. Hereinafter, pulverized product after drying is referred to as irregular crushed product in Examples based on the shape thereof.

The aforementioned water absorbing resin obtained in the present invention is preferably adjusted to have the particle size as described above. More preferably, this water absorbing resin has a centrifuge retention capacity (CRC) for a physiological saline solution before the surface crosslinking of not less than 28 g/g, more preferably 30 to 70 g/g, more preferably 30 to 60 g/g, and particularly preferably 35 to 60 g/g. Regulation of the absorption capacity may be carried out through controlling the aforementioned polymerization conditions such as the internal crosslinking agent, and drying conditions.

(12) Surface Crosslinking Treatment

The particulate water absorbing agent used in the present invention can be obtained preferably by adjusting to have a certain particle size, and further subjecting thus resulting crosslinked polymer particles having a certain absorption capacity to surface crosslinking. For example, the particulate water absorbing agent used in the present invention is obtained through lowering its absorption capacity (CRC) by such surface crosslinking. More preferably, the particulate water absorbing agent used in the present invention is obtained by lowering the absorption capacity (CRC) by the surface crosslinking to 95 to 50%, and still more 90 to 60% compared with the value before the surface crosslinking. Degree of the lowering of the absorption capacity may be adjusted ad libitum depending on the kind and amount of the crosslinking agent, reaction temperature in the surface crosslinking, time period required for the surface crosslinking reaction and the like.

Moreover, the "plus frictional charge" may be regulated by combination of the particular water absorbing resin and the particular surface crosslinking agent. When the aforementioned polyacrylate is used as the water absorbing resin, for example, an epoxy compound, alkylene carbonate, a polyvalent metal may be used as the surface crosslinking agent for giving "plus frictional charge", however, other surface crosslinking agent may be also used in the range to give "plus frictional charge".

The surface crosslinking agent which may be used in the present invention is not particularly limited, but for example, any surface crosslinking agent illustrated in U.S. Pat. Nos. 6,228,930, 6,071,976, 6,254,990 and the like can be used.

Examples of the surface crosslinking agent which may be used in the present invention include e.g., epoxy compounds such as ethylene glycol diglycidyl ether and glycidol; polyvalent amine compounds such as ethylenediamine, diethylenetriamine, triethylenetetramine, tetraethylenepentamine, pentaethylenehexamine, polyethyleneimine and polyamide polyamine; haloepoxy compounds such as epichlorohydrin, epibromohydrin and α-methylepichlorohydrin; condensates of the aforementioned polyvalent amine compound and the aforementioned haloepoxy compound (U.S. Pat. Nos. 4,755, 562, 4,824,901); oxazolidinone compounds such as 2-oxazolidinone (U.S. Pat. Nos. 6,472,478, 6,503,978); alkylene carbonate compounds such as ethylene carbonate (U.S. Pat. No. 5,409,771); polyvalent metal compounds such as aluminum salts and zirconium (European Patent No. 1516884, International Publication No. WO2004/069915), and the like. These may be used alone, or two or more thereof may be used in combination in the range to exhibit the "plus frictional charge".

Examples of the surface crosslinking agent which can be used other than those described hereinabove include polyhydric alcohol compounds such as mono-, di, tri, tetra- or polyethylene glycol, monopropylene glycol, 1,3-propanediol, dipropylene glycol, 2,3,4-trimethyl-1,3-pentanediol, polypropylene glycol, glycerin, polyglycerin, 2-butene-1,4-diol, 1,4-butanediol, 1,3-butanediol, 1,5-pentanediol, 1,6-hexanediol and 1,2-cyclohexanedimethanol.

To sufficiently achieve the advantage of the present invention, it is preferred that polyhydric alcohol among these surface crosslinking agents is essentially used in combination or alone. The polyhydric alcohol has preferably 2 to 10 carbon atoms, and more preferably 3 to 8 carbon atoms.

Using amount of the surface crosslinking agent may vary depending on the used compound, combination thereof and the like, but may fall within the range of preferably 0.001 to 10% by weight, and more preferably 0.01 to 5% by weight of the water absorbing resin.

When surface crosslinking is carried out in the present invention, water is preferably used. In this process, the amount of water which may be used may vary depending on the moisture content of the used water absorbing resin, but preferably falls within the range of 0.5 to 20% by weight, and more preferably falls within the range of 0.5 to 10% by weight of the water absorbing resin. Furthermore, a hydrophilic organic solvent may be used in addition to water. When the hydrophilic organic solvent is used, using amount thereof falls within the range of 0 to 10% by weight, more preferably within the range of 0 to 5% by weight, and still more preferably within the range of 0 to 3% by weight of the water absorbing resin.

When the surface crosslinking is carried out in the present invention, preferable method is premixing of water and/or a hydrophilic organic solvent with a surface crosslinking agent, followed by spraying or drop-wise addition of the aqueous solution to the water absorbing resin, and the spraying method is more preferable. Droplet size to be sprayed falls, as average particle diameter, preferably within the range of 0.1 to 300 μm, and more preferably within the range of 0.1 to 200 μm.

As mixing equipment used in mixing the water absorbing resin, the surface crosslinking agent, and water and/or the hydrophilic organic solvent, those having strong mixing force are preferable for homogenously and intimately mixing these materials. Suitable examples of the mixing equipment include e.g., a cylinder type mixer, a double wall conical mixer, a high speed agitation type mixer, a v-shaped mixer, a ribbon type mixer, a screw type mixer, a double-arm kneader, a crashing type kneader, a rotation type mixer, an air-flow type mixer, a turbulizer, a batch type Lodige mixer, a continuous type Lodige mixer and the like.

The water absorbing resin after mixing with the surface crosslinking agent is preferably subjected to a heat treatment. Heating temperature (heating medium temperature or material temperature/particularly, heating medium temperature) preferably falls within the range of 100 to 250° C., and more within the range of preferably 150 to 250° C. Heating time preferably falls within the range of 1 min to 2 hrs. Examples of suitable combination of the heating temperature and the heating time include at 180° C. for 0.1 to 1.5 hrs, and at 200° C. for 0.1 to 1 hour.

(13) Moisture Content

The water absorbing resin obtained by the above surface crosslinking is subjected to a potent heating treatment (heating at a high temperature for a long time period as described above) in the surface crosslinking treatment for improving the absorbency against pressure (AAP). Hence, the water absorbing resin obtained by the above surface crosslinking is generally dried to give the moisture content of not greater than 1%. The water absorbing resin obtained by the above surface crosslinking has: (a) centrifuge retention capacity (CRC) for a 0.90% by weight aqueous sodium chloride solution being 28 to 50 g/g; (b) absorbency against pressure measured with 0.90 g of the particulate water absorbing agent (AAP: 0.90 g) for a 0.90% by weight aqueous sodium chloride solution under a pressure of 4.8 kPa for 60 min being 20 to 40 g/g; (d) positive frictional charge when dried to give the moisture content of not higher than 0.5% by weight; and (e) permeability potential under pressure (PPUP) being 60 to 100% specified by the following formula (I):

$$\text{PPUP}(\%) = (\text{AAP: } 5.0 \text{ g})/(\text{AAP: } 0.90 \text{ g}) * 100 \qquad (I)$$

wherein (AAP: 0.90 g) is the absorbency against pressure measured with 0.90 g of the particulate water absorbing agent for a 0.90% by weight aqueous sodium chloride solution under a pressure of 4.8 kPa for 60 min; and (AAP: 5.0 g) is the absorbency against pressure measured with 5.0 g of the particulate water absorbing agent for a 0.90% by weight aqueous sodium chloride solution under a pressure of 4.8 kPa for 60 min.

Such a particulate water absorbing agent has the aforementioned characteristics (a), (b), (d) and (e), and in particular, has a novel feature of the permeability potential under pressure (PPUP) being not less than 60% but not more than 100%. However, according to the present invention, (c) the moisture content is further adjusted to be 2 to 10% by weight, still further, to fall within the range of the moisture content as described later (15).

In order to obtain the particulate water absorbing agent of the present invention, the moisture content in the surface crosslinking reaction may be regulated to be 2 to 10% by weight, or the moisture content according to the present invention (2 to 10% by weight) may be provided by drying or adding water after the surface crosslinking. However, for certainly achieving the physical properties according to the present invention, it is preferred that heating is conducted to give the moisture content of not higher than 1% by weight in the surface crosslinking, and further, remoisturization is executed after the surface crosslinking to give the moisture content of 2 to 10% by weight. In such remoisturization, agglomeration is more preferably conducted using water as a binder.

Accordingly, the method for the production of the particulate water absorbing agent of the present invention preferably includes an agglomeration step. This agglomeration step is a step of heating after the surface treatment while keeping the moisture content of 2 to 10% by weight by adding water followed by pulverization as needed. According to this agglomeration step, adjustment to give certain particle size as powder may be performed. Whether or not the agglomeration was perfected can be readily discriminated by increase in average particle diameter (for example, 1.01 to 2 times), or decrease in the amount of fine powder of not greater than 150 μm.

In the water to be added may include a chelating agent, a plant component, an antimicrobial, a water soluble polymer, an inorganic salt and the like described later. It is preferred that content of these additives may fall within the range of 0.001 to 50% by weight as the concentration in the aqueous solution.

In the present invention, preferable method for regulating the moisture content is spraying or drop-wise addition of water or the aqueous solution thereof to the water absorbing resin, and the spraying method is more preferable. Droplet size to be sprayed falls, as average particle diameter, preferably within the range of 0.1 to 300 μm, and more preferably within the range of 0.1 to 200 μm. As the apparatus for adding water, any of the aforementioned apparatus for adding the surface crosslinking agent can be used.

For achieving homogenous addition and permeation of water, and further for improving the powder flowability, preferably, a heat treatment is carried out after mixing with water or the aqueous solution thereof. Preferably, in the heat treatment, the heating is carried out while keeping the moisture content of 2 to 10% by weight. A part of water may be volatilized during the heat treatment as long as the moisture content is kept 2 to 10% by weight.

For the heating, a heating medium such as hot air is used, and the heating temperature (heating medium temperature or material temperature) may be preferably 40 to 120° C., and more preferably 50 to 100° C. The heating time may be preferably 1 min to 2 hrs. The heating may be preferably carried out while standing still (without stirring) to permit hardening (loose block shape). Preferably, in heating, hardening may be allowed by heating the water absorbing resin added with water after heaping to give approximately 1 to 100 cm, more preferably 5 to 80 cm, and particularly preferably 10 to 70 cm. Thus hardened water absorbing resin is then pulverized, and preferably classified to obtain intended particulate water absorbing agent of the present invention.

(14) Other Additives

In the present invention, the (A1) plant components, (B1) polyvalent metal salts of organic acids, (C1) inorganic fine particles (including (D1) composite hydrated oxides) and the like described below may be also added as minor components in addition to the aforementioned chelating agent, by which various functions can be imparted to the particulate water absorbing agent of the present invention.

Although using amount of these additives (A1) to (D1), and (E1) and (F1) may vary depending on the object and function to be imparted, exemplary amount of adding one of them falls within the range of generally 0 to 10 parts by weight, preferably 0.001 to 5 parts by weight, and more preferably 0.002 to 3 parts by weight based on 100 parts by weight of the water absorbing resin. In general, the amount of less than 0.001 parts by weight does not provide sufficient effect or additional function, while the amount beyond 10 parts by weight may not achieve effect to meet with the added amount, or may deteriorate absorbing performance.

(A1) Plant Component

A plant component can be incorporated in the particulate water absorbing agent according to the present invention for achieving deodorization effect. Preferable proportion of this plant component to be incorporated is as described above.

The plant component which can be used in the present invention is preferably powder of a plant per se or an extract from a plant. Compound included in this plant component is preferably at least one compound selected from polyphenol, flavone, derivatives thereof and caffeine, or at least one compound selected from tannin, tannic acid, stachyurus praecox, gall and gallic acid. For example, the compounds are illustrated in U.S. Pat. No. 6,469,080, European Patent No. 1352927 and International Publication No. WO2003/104349. Examples of the form of the plant component which can be incorporated in the present invention include plant extracts (essential oils and the like), plants themselves (plant-ground powder and the like), plant residues or extract residues as by-products generated in production steps from plant processing industry or foods processing industry, and the like.

Additionally, particle size of the powder when the plant component (A1) is powder, and/or particle size of powder carrying an extract (essential oil) that contains the plant component (A1) extracted from a plant is generally 0.001 to 1000 µm, and preferably 1 to 600 µm. Weight average particle diameter (M1) of the particles including the plant component is preferably not greater than 500 µm, and more preferably not greater than 300 µm. When this weight average particle diameter (M1) is greater than 500 µm, effects of the active ingredient included in the plant component upon contact with urine may be insufficient. Thus, stable deodorization performance may not be exerted. Additionally, in light of imparting excellent deodorization performance and stability, this weight average particle diameter (M1) is preferably smaller than the weight average particle diameter of the water absorbing resin. Examples of the particle containing a plant component include plant powder yielded from a plant per se, supported material having a particulate form that supports a plant component, and the like. Examples of this supported material include those supporting an extract (essential oil) containing a plant component extracted from a plant. In light of ease in adding to the aforementioned water absorbing resin, the plant component which can be used in the present invention preferably may be a liquid and/or aqueous solution state at an ordinary temperature.

(B1) Polyvalent Metal Salt of Organic Acid

For improving the powder characteristics, use of a polyvalent metal salt illustrated in International Publication No. WO2004/069936 is preferred.

(C1) Inorganic Fine Particle

To prevent blocking in moisture absorption, an inorganic fine particle, in particular, an inorganic fine particle of non-dissolving in water may be added to the particulate water absorbing agent according to the present invention. Specific examples of inorganic powder to be used include e.g., metal oxides such as silicon dioxide, titanium oxide and the like; silica acid (silicate salt) such as natural zeolite, synthetic zeolite and the like; kaolin, talc, clay, bentonite, and the like. Among these, silicon dioxide and silica acid (silicate salt) are more preferable, and silicon dioxide and silica acid (silicate salt) with average particle diameter, measured by a coulter counter method, of 0.001 to 200 µm are further preferable.

(D1) Composite Hydrated Oxide

To allow excellent flowability after moisture absorption and excellent deodorization performance to be achieved, to the particulate water absorbing agent according to the present invention may be added a composite hydrated oxide containing zinc and silicon, or zinc and aluminum (for example, illustrated in International Publication No. WO2005/010102)

(E1) Addition of Chelating Agent

In order to obtain the particulate water absorbing agent of the present invention, preferably a chelating agent, and particularly a polyvalent carboxylic acid and a salt thereof may be incorporated.

The chelating agent which may be used in the particulate water absorbing agent of the present invention is preferably a chelating agent with high sequestering ability or chelating ability for Fe or Cu, and specifically, a chelating agent with stability constant for Fe ion of not lower than 10, preferably not lower than 20. The chelating agent is further preferably an aminopolyvalent carboxylic acid and salts thereof, and particularly preferably an aminocarboxylic acid having 3 or more carboxyl groups and salts thereof.

Specific examples of these polyvalent carboxylic acids include diethylenetriamine pentaacetic acid, triethylenetetramine hexaacetic acid, cyclohexane-1,2-diamine tetraacetic acid, N-hydroxyethyl ethylenediamine triacetic acid, ethylene glycol diethyl ether diamine tetraacetic acid, ethylenediamine tetrapropionic acetic acid, N-alkyl-N'-carboxymethyl aspartic acid, N-alkenyl-N'-carboxymethyl aspartic acid and alkaline metal salts alkaline earth metal salts, ammonium salts or amine salts thereof. Among these, diethylenetriamine pentaacetic acid, triethylenetetramine hexaacetic acid, N-hydroxyethyl ethylenediamine triacetic acid and salts thereof are most preferable.

(F1) Others

Other additives such as an antimicrobial, an aqueous polymer, a water insoluble polymer, water, a surfactant, an organic fine particle, and the like may be added arbitrarily, as long as the particulate water absorbing agent of the present invention can be especially obtained.

(15) Particulate Water Absorbing Agent of the Present Invention

The particulate water absorbing agent of the present invention obtained by the aforementioned method for the production as an example, is a novel particulate water absorbing agent exhibiting novel performance not conventionally available.

That is, the particulate water absorbing agent of the present invention comprises: (A) a water-swelling crosslinked polymer having a constitutional unit derived from an unsaturated monomer containing an acid group and/or a salt thereof; and (B) water, and the particulate water absorbing agent having:

(a) centrifuge retention capacity (CRC) for a 0.90% by weight aqueous sodium chloride solution being 28 to 50 g/g;

(b) absorbency against pressure (AAP: 0.90 g) being 20 to 40 g/g;

(c) moisture content determined on the basis of the weight loss in drying at 105° C. for 3 hrs being 2 to 10% by weight;

(d) positive frictional charge when the moisture content determined on the basis of the weight loss in drying at 105° C. for 3 hrs is not higher than 0.5% by weight; and (e) permeability potential under pressure (PPUP) being 60 to 100% specified by the following formula (I):

$$PPUP(\%) = (AAP: 5.0\ g)/(AAP: 0.90\ g) * 100 \qquad (I)$$

wherein (AAP: 0.90 g) is the absorbency against pressure measured with 0.90 g of the particulate water absorbing agent for a 0.90% by weight aqueous sodium chloride solution under a pressure of 4.8 kPa for 60 min; and (AAP: 5.0 g) is the absorbency against pressure measured with 5.0 g of the particulate water absorbing agent for a 0.90% by weight aqueous sodium chloride solution under a pressure of 4.8 kPa for 60 min.

The particulate water absorbing agent of the present invention exerts a particularly marked effect in production of absorbent cores or absorbing articles. Preferably, the particulate water absorbing agent of the present invention is a particulate water absorbing agent for use in absorbent cores or absorbing articles. Preferably, the particulate water absorbing agent of the present invention is a particulate water absorbing agent for use in absorbent cores for sanitary goods or absorbing articles having such as absorbent core. Preferably, the particulate water absorbing agent of the present invention is a particulate water absorbing agent for use in sanitary goods such as diapers.

The particulate water absorbing agent of the present invention has (a) a centrifuge retention capacity (CRC) of 28 to 50 g/g, preferably 28 to 45 g/g, still more preferably 30 to 45 g/g, and particularly preferably 30 to 40 g/g. When the CRC is too great, other physical properties not specified in the present invention such as gel strength and resistance to urine may be deteriorated. In contrast, when the CRC is too low, absorption capacity may be insufficient for diapers in practical applications.

The particulate water absorbing agent of the present invention has (b) an absorbency against pressure measured with 0.90 g (AAP: 0.90 μg) of 20 to 40 g/g, preferably 20 to 35 g/g, more preferably 20 to 33 g/g, and particularly preferably 20 to 30 g/g. Too high AAP: 0.90 g may result in inferior balance in terms of the production cost, while too low AAP: 0.90 g may result in insufficient absorption capacity for diapers in practical applications.

The particulate water absorbing agent of the present invention has (c) a moisture content of essentially 2 to 10% by weight, preferably 2 to 8% by weight, more preferably 2 to 7% by weight, still more preferably 2 to 6% by weight, and particularly preferably 2 to 5% by weight. When the moisture content is out of the above range, absorption performance may be deteriorated, and a water absorbing agent that is inferior in powder characteristics (flowability, conveying property, damage resistance) may be provided. By setting the (c) moisture content to fall within the above range, and by specifying other characteristics such as frictional charge as described above, diapers and the like can be continuously produced with stable absorption performances and less variation of the amount of the water absorbing agent, in production step of diapers and the like. The (c) moisture content of this particulate water absorbing agent may be a moisture content before use for production of an absorbent core or an absorbing article (diaper or the like). Alternatively, the (c) moisture content of this particulate water absorbing agent may be a moisture content in use for production of an absorbent core or an absorbing article (diaper or the like) For example, in the step of distribution of diapers, the particulate water absorbing agent in this diaper usually absorbs moisture. Owing to this moisture absorption, moisture content of the particulate water absorbing agent removed from the diaper following distribution becomes higher than the moisture content of the particulate water absorbing agent in the diaper immediately after the production (before the distribution).

The particulate water absorbing agent of the present invention has (d) a positive (plus) frictional charge when the moisture content upon drying is not higher than 0.5% by weight. When the frictional charge is a negative (minus) charge, absorption performances (CRC, AAP, PPUP) desired for diapers in practical applications cannot be achieved, and physical properties that meet the absorption performances may not be exhibited in the diaper.

The particulate water absorbing agent of the present invention has (e) a permeability potential under pressure (PPUP) of 60 to 100%, preferably 65 to 100%, and particularly preferably 70 to 100%.

(16) Other Characteristics of Particulate Water Absorbing Agent of the Present Invention (f) Conveying Speed Stability Index The particulate water absorbing agent of the present invention has a conveying speed stability index of 0 to 4.0%, preferably 0 to 3.5%, more preferably 0 to 3.0%, and particularly preferably 0 to 2.5%. When the conveying speed stability index is greater than 4.0%, for example, in actual continuous production of diapers and the like, fluctuation (variance) of the amount of the water absorbing resin (or particulate water absorbing agent) included per one piece of the diaper may be increased. Consequently, variance may be also caused in absorption performance of the diaper per se, thereby possibly failing to continuously produce the diapers with stable absorption performance. The same is true of continuous production of absorbing articles other than diapers. Although lower limit is not particularly restricted, in consideration of the rise in const due to difficulty in the production, the conveying speed stability index is preferably not less than 0.01%. The conveying speed stability index falling within the aforementioned range can be accomplished by, for example, the certain particle size and the certain moisture content as described above, and the frictional charge being a positive charge (plus).

(g1) Particles of 600 to 150 μm; (h1) Logarithmic Standard Deviation

Bulk density (specified by JIS K-3362) of the particulate water absorbing agent the present invention is adjusted to fall within the range of preferably 0.40 to 0.90 g/ml and more preferably 0.50 to 0.80 g/ml. Further, according to the particulate water absorbing agent of the present invention, (g1) particles having a diameter in between 600 and 150 μm account for 60 to 100% by weight, more preferably 70 to 100% by weight, and further preferably 80 to 100% by weight of the total. The particulate water absorbing agent of the present invention has a weight average particle diameter of preferably 200 to 500 μm, more preferably 250 to 500 μm, and still more preferably 300 to 500 μm. In the particulate water absorbing agent of the present invention, particles having a diameter of not smaller than 150 μm account for preferably 90 to 100% by weight of the total, more preferably 93 to 100% by weight of the total, and still more preferably 95 to 100% by weight of the total. Logarithmic standard deviation ($\sigma\zeta$) of particle size distribution (h1) in the particulate water absorbing agent of the present invention may be preferably 0.20 to 0.50, more preferably 0.20 to 0.45, and particularly preferably 0.20 to 0.40. Out of the preferable range, use in an absorbent core may not achieve the advantage of the present invention. Particle size and particle size distribution of the particulate water absorbing agent can be adjusted ad libitum through pulverization, classification, agglomeration, fine powder recovery and the like.

(17) Absorbent Core

The particulate water absorbing agent of the present invention usually has a particulate shape. By forming together with other arbitrary absorption material, the absorbent core (formed product) of the present invention can be obtained. Shape of the absorbent core is not particularly limited, but may be processed preferably into the sheet-like, cylindrical, film-like or fibrous form, particularly preferably into sheet-like form (may be also referred to as web form) to provide an absorbent core.

In order to achieve the advantage of the present invention, the absorbent core may include the particulate water absorbing agent according to the present invention and hydrophilic fibers. The hydrophilic fiber which can be used in the present invention is not particularly limited, but in general, any hydrophilic fiber having a negative charge (minus) measured according to the measurement method described later is preferred. Illustrative examples of the hydrophilic fiber include e.g., ground wood pulp, as well as cotton linters, crosslinked cellulosic fibers, rayon fibers, cotton fibers, wool fibers, acetate fibers, vinylon fibers, and the like, which may be preferably airlied.

When the absorbent core according to the present invention is an absorbent core including the particulate water absorbing agent and the hydrophilic fibers, content of the particulate water absorbing agent (generally referred to as core concentration) based on total weight of the particulate water absorbing agent and the hydrophilic fibers preferably falls within the range of 20 to 100% by weight, more preferably the range of 25 to 90% by weight, and still more preferably the range of 30 to 80% by weight. Such absorbent cores are preferably subjected to formation under compression to give the density in the range of 0.001 to 0.50 g/cc, and the basis weight in the range of 0.01 to 0.20 g/cm².

(18) Absorbing Article

The absorbing article (final consumer goods) according to the present invention is equipped with the aforementioned absorbent core of the present invention, a surface sheet with liquid permeability and a back sheet with liquid impermeability. Although the method for the production of the absorbing article according to the present invention is not particularly limited, but for example, absorbing articles such as e.g., disposable diapers or sanitary napkin may be formed by sandwiching the absorbent core between a substrate with liquid permeability (the surface sheet) and a substrate with liquid impermeability (the back sheet), and mounting an elastic part, a diffusion layers, a pressure sensitive adhesive tape and the like as needed.

The particulate water absorbing agent and the absorbent core according to the present invention can impart high absorption performance to absorbing articles, and exhibits excellent absorption performance and absorption properties for a long period of time.

EXAMPLES

The present invention will be explained specifically by way of Examples and Comparative Examples below, but the present invention is not limited thereto.

Various performances of a water absorbing resin, a particulate water absorbing agent (hereinafter, abbreviated as particulate water absorbing agent) and an absorbing article were determined by the following methods. Electrical equipments were always used under conditions of 100 V and 60 Hz in Examples. In addition, the water absorbing resin, the particulate water absorbing agent and the absorbing article were used under conditions of 25° C.±2° C. and 50% RH (relative humidity), unless particularly specified. An aqueous solution of 0.90% by weight of sodium chloride was used as a physiological saline solution. Also, measurement of the absorbency was performed with the solid content of the water absorbing resin of 95±3%.

(a) Centrifuge Retention Capacity (CRC) for 0.90% by Weight Aqueous Sodium Chloride Solution A water absorbing resin (or particulate water absorbing agent) of 0.20 g was uniformly put in a bag (60 mm×85 mm) made of unwoven fabric and immersed in a physiological saline solution controlled at 25±2° C. The bag was taken out of the saline solution 30 minutes later and subjected to dewatering for 3 minutes at 250 G (250×9.81 m/sec²) using a centrifuge (Model H-122 small size centrifuge manufactured by Kokusan Corporation) and then weighed to determine weight $W_2$ (g) of the bag. In addition, weight $W_1$ (g) of the bag then was measured after carrying out a similar operation without using any water absorbing resin (or particulate water absorbing agent). Centrifuge retention capacity (g/g) was then calculated from the weights $W_1$ (g) and the weight and $W_2$ (g) according to the following formula:

Centrifuge retention capacity(g/g)=$(W_2-W_1)$/weight of water absorbing resin(or particulate water absorbing agent)(g)−1=$[(W_2-W_1)/0.20]$−1.

(b) Absorbency Against Pressure (AAP: 0.90 g) for a 0.90% by Weight Aqueous Sodium Chloride Solution under Pressure of 4.8 kPa A water absorbing resin (or particulate water absorbing agent) of 0.900 g was uniformly scattered on a 400-Mesh wire mesh made of stainless steel (mesh opening size: 38 μm) welded to the bottom end face of a plastic support cylinder with an inner diameter of 60 mm. A piston (cover plate), which has an outer diameter a little smaller than 60 mm, forms no gap against the inner surface of the support cylinder and can move up and down smoothly, was mounted on the water absorbing agent. Total weight $W_3$ (g) of the support cylinder, the water absorbing resin (or particulate water absorbing agent) and the piston was measured. The weight $W_3$ (g) is a total weight derived by adding the weight of the support cylinder, the weight of the water absorbing resin (or particulate water absorbing agent) and the weight of the piston. A load adjusted to apply a pressure of 4.8 kPa including the piston on the water absorbing resin (or particulate water absorbing agent) uniformly was mounted on the piston, thereby completing a set of measuring apparatus. A glass filter having a diameter of 90 mm and a thickness of 5 mm was placed in a Petri dish having a diameter of 150 mm, and a physiological saline solution controlled at 25±2° C. was poured up to the same level as the upper surface of the glass filter. A sheet of filter paper having a diameter of 9 cm (No. 2, manufactured by Toyo Roshi Kaisha Ltd.) was placed thereon to be entirely wetted, and then excess solution was removed.

The set of the measuring apparatus was placed on the wetted filter paper and the liquid absorption was allowed under the load. The liquid level was kept constant by adding the liquid when the liquid surface became lower than the upper surface of the glass filter. The set of the measuring apparatus was lifted up after an hour and weight $W_4$ (g) (the total weight of the support cylinder, the swollen water absorbing resin (or particulate water absorbing agent) and the piston) excluding the load was measured again. Thus, the absorbency against pressure (g/g) was calculated from the weights $W_3$ and $W_4$ according to the following formula:

Absorbency Against Pressure(AAP: 0.90 g)(g/g)=$(W_4-W_3)$/weight of water absorbing resin(or particulate water absorbing agent)(g)=$(W_4-W_3)/0.900$.

(c) Permeability Potential Under Pressure (PPUP)

Value of the absorbency against pressure (AAP: 5.0 g) was determined by a similar operation to the measurement of (b) absorbency against pressure (AAP: 0.90 g), except that the amount of the water absorbing resin (or particulate water absorbing agent) was changed from 0.900 g to 5.000 g. In this operation, samples having high absorbency against pressure (AAP: 5.0 g) can result in extremely high level of the swollen water absorbing resin (or particulate water absorbing agent) layer, therefore, the support cylinder for use must afford enough height. Using the absorbencies against pressure (AAP: 0.90 g) and (AAP: 5.0 g) determined by the operation described above, permeability potential under pressure (PPUP) can be determined by the following formula:

Permeability Potential Under Pressure(PPUP)(%)= (AAP: 5.0 g(g/g)/AAP: 0.90 g(g/g))×100.

(d) Moisture Content of Water Absorbing Resin (or Particulate Water Absorbing Agent)

Fundamental operation followed the measurement method described in EDANA (EUROPEAN DISPOSABLES AND NONWOVENS ASSOCIATION), RECOMMENDED TEST METHOD, 430. 1-99, (i.e., heating in a windless oven at 105° C. for 3 hrs, and calculating on the basis of the weight loss in drying).

(e) Frictional Charge

The water absorbing resin (or particulate water absorbing agent) in an amount of 25 g which had been dried such that the moisture content determined by the measurement method described in above (d) became less than 0.5% by weight was charged in a glass screw tube (manufactured by Maruemu Co., Ltd., screw tube No. 7, aperture internal diameter×body diameter×height=φ23 mm×φ35 mm×78 mm, cap: made of polypropylene, packing: heat resistant high sheet), and sealed.

This screw tube hermetically including the water absorbing resin (or particulate water absorbing agent) was continuously shaken for 20 seconds. This operation of shaking may be conducted either mechanically or manually. Conditions for carrying out the shaking may be at a frequency of 3 to 5 times per second with the amplitude of the vibration of 10 to 20 cm. This shaking must be conducted such that the water absorbing resin (or particulate water absorbing agent) in the screw tube moves as broadly and fast as possible.

After shaking for 20 seconds, the water absorbing resin (or particulate water absorbing agent) in the screw tube was immediately spread on a sheet, and the electric potential of the water absorbing resin (or particulate water absorbing agent) was measured using a non-contact electrostatic field meter (product name: Simco Electrostatic Field Meter FMX-002, manufactured by Simco Japan Company, Inc.) according to a manual provided by the manufacturer and attached to the meter. Measurement of the electric potential was completed within 15 seconds after spreading the water absorbing resin (or particulate water absorbing agent) on the sheet. Furthermore, as described in the aforementioned manual, distance between the electrostatic field meter and the water absorbing resin (or particulate water absorbing agent) upon the measurement shall be 25 mm±1 mm. At this measurement time point within 15 seconds, electric potential displayed on the electrostatic field meter was quickly read. When thus read electric potential was a plus potential, the frictional charge was decided as positive charge, while when thus read electric potential was a minus potential, the frictional charge was decided as negative charge. More specifically, when the electric potential displayed on the aforementioned electrostatic field meter falls within the range of +0.01 to +20.00 kv, the frictional charge was decided as positive charge. In contrast, when the electric potential displayed on the aforementioned electrostatic field meter falls within the range of −0.01 to −20.00 kv, the frictional charge was decided as negative charge. In light of lowering of the conveying speed stability index, the aforementioned electric potential observed in the measurement of the frictional charge is preferably not less than +0.01 kv but not greater than +10.0 kv, and more preferably not less than +0.01 kv but not greater than +5.00 kv.

As a sheet used in the measurement as described above, a piece of a glove manufactured by Showa Co. (trade name: Vinitop, thick; material (obverse side): vinyl chloride resin (non phthalate ester based plasticizer), material (reverse side): rayon (flocked)) cut into the size of 12 cm×12 cm was used. When the water absorbing resin (or particulate water absorbing agent) was spread on the sheet, the obvere side of the glove was used as the upper face of the sheet, and the water absorbing resin (or particulate water absorbing agent) was spread on the upper face of this sheet to heap up but not to spill out from the sheet. In this state, frictional charge was measured. This heaping state refers to, for example, a state in which the water absorbing resin (or particulate water absorbing agent) spread on the sheet forms a substantially cone shape having a height of 2 to 4 cm and a diameter of the bottom face of 7 to 12 cm. Moreover, the measurement of this frictional charge was conducted in a room in which regulation of the room temperature at 23±2° C., and the relative humidity at 40±3% RH was executed. Also, because the water absorbing resin (or particulate water absorbing agent) used in this measurement should have a moisture content of less than 0.5%, in case of the water absorbing resin (or particulate water absorbing agent) having a moisture content of not less than 0.5% by weight, the frictional charge should be measured after lowering the moisture content through drying ad libitum. For lowering the moisture content of the water absorbing resin (or particulate water absorbing agent) to less than 0.5% by weight, the drying temperature may be preferably 180±3° C. as the preset temperature of the dryer to be used. It is preferred that drying time for lowering the moisture content of the water absorbing resin (or particulate water absorbing agent) to less than 0.5% by weight is 1 hour.

(f) Conveying Speed Stability Index (SI Value)

Measurement of conveying speed of the water absorbing resin (or particulate water absorbing agent) is carried out using DRY MATERIAL FEEDER (product name: ACCU-RATE 300, manufactured by KUMA engineering Co., LTD.). With regard to size and the like of the screw part which may be employed, they may be as follows: entire length of screw part: 30 cm, screw pitch: 2 cm, screw shape: 4 mm (width in horizontal direction)×4.5 mm (width in direction of rotation axis), external diameter: 2.6 cm, and material of screw: SUS304, spring type screw. The pipe may be made of SUS304, and the pipe may have an internal diameter of 2.9 cm, with the length of the pipe being adjusted for use to just fit the screw. The water absorbing resin (or particulate water absorbing agent) in an amount of 5 kg is charged into a hopper of the feeder. Rotational frequency of the screw is set to be 96 rpm. For rendering the rotational frequency of the screw be 96 rpm, setting memory of the screw apparatus may be 900. However, control with a memory may possibly result in some deviance in the rotational frequency depending on the employed equipment, therefore, control with the rotational frequency is preferred upon the measurement. After stabilization of feed of the water absorbing resin (or particulate water absorbing agent), measurement of the conveying amount is started. Stabilization of the feed will be attained in about 20 seconds or longer following starting the rotation of the screw. The conveying amount (g) of the water absorbing resin (or particulate water absorbing agent) is measured every 30 seconds after starting the measurement for a period of 5 minutes (measurement point: 10 points). Thus, conveying speed (g/s) at each time is determined by calculation. From the resulting data of the conveying speed (g/s) at the ten points, standard deviation σ is determined. Conveying speed stability index, SI value (%), is determined from thus resulting standard deviation σ and mean value $F_{ave}$ of the conveying speed at the ten points according to the following formula:

Conveying speed stability index(SI value)(%)=σ/$F_{ave}$×100.

(g) Mass (Weight) Median Particle Size (D50) Specified by Standard Sieve Classification and Logarithmic Standard Deviation (σζ) Specified by Standard Sieve Classification According to International Publication No. WO2004/069404, the water absorbing resin (or particulate water absorbing agent) was subjected to sieving using JIS standard sieves having mesh opening size of 850 μm, 710 μm, 600 μm, 500 μm, 425 μm, 300 μm, 212 μm, 150 μm, 106 μm and 45 μm (JIS Z8801-1 (2000)) or sieves in conformity thereto, and oversize percentages R were plotted on a logarithmic probability paper. Particle size corresponding to R=50% by weight was thus determined as mass median particle size (D50). Logarithmic standard deviation (σζ) is represented by the following formula, wherein smaller value of σζ means narrower particle-size distribution:

$$\sigma\zeta = 0.5 \times \ln(X_2/X_1)$$

(wherein $X_1$ and $X_2$ are particle diameters for R=84.1% and R=15.9%, respectively).

(h) Evaluation of Absorbent Core Performance

An absorbent core was produced using the water absorbing resin (or particulate water absorbing agent) described later and subjected to a rewet test in order to evaluate performances as an absorbent core.

To begin with, a method for production of an absorbent core for evaluation is demonstrated below.

The water absorbing resin (or particulate water absorbing agent) described later in an amount of 2 parts by weight and 2 parts by weight of crushed wood pulp were subjected to dry mixing using a mixer. Thus obtained mixture was then spread on a wire screen of 400-Mesh (mesh opening size: 38 μm) to form a web with a diameter of 90 mm. The web was pressed under a pressure of 196.14 kPa (2 kgf/cm²) for 1 minute to obtain an absorbent core for evaluation with a basis weight of 0.06 g/cm².

Subsequently, a method for evaluation of rewet amount is demonstrated below.

The absorbent core for evaluation was placed on the bottom of a Petri dish with an inner diameter of 90 mm made of stainless steel (SUS), and nonwoven fabric with a diameter of 90 mm was placed on this absorbent core for evaluation. Next, a piston and a load adjusted so as to press with a pressure of 4.8 kPa uniformly the absorbent core were placed on this nonwoven fabric. The piston and the load employed were equipped with a liquid charging inlet having a diameter of 5 mm at the center portion thereof. Then, 25 ml of a physiological saline solution (0.90% by weight aqueous sodium chloride solution) was poured onto the central portion of the absorbent core for evaluation from the aforementioned liquid charging inlet thereby allowing the absorbent core for evaluation to absorb the liquid. Thirty minutes later, 25 ml of a physiological saline solution (0.90% by weight aqueous sodium chloride solution) was further poured onto the central portion of the absorbent core for evaluation from the aforementioned liquid charging inlet thereby allowing the absorbent core for evaluation to absorb the liquid for additional 30 min. Following this liquid absorption for 30 min, the piston and the load adjusted so as to press with a pressure of 4.8 kPa uniformly the absorbent core were removed, and 30 sheets of filter paper having an external diameter of 90 mm (manufactured by Toyo Roshi Kaisha, Ltd., No. 2) total weight of which ($W_7$ (g)) had been measured beforehand were placed on the absorbent core for evaluation. Further, a piston and a load (total weight of the piston and the load being 20 kg) with an external diameter of 90 mm, which apply the pressure uniformly on the absorbent core, the nonwoven and the filter paper, were quickly placed on the filter paper. Thus, absorption of rewet liquid into the filter paper was permitted through applying the pressure for 5 minutes. Weight of the 30 sheets of the filter paper ($W_8$ (g)) was then measured to determine the rewet amount according to the following formula:

$$\text{Rewet amount}(g) = W_8(g) - W_7(g).$$

Reference Example 1

In 5500 g of an aqueous solution of sodium acrylate having a neutralization ratio of 75% by mole (monomer concentration: 38% by weight) was dissolved 4.9 g of polyethylene glycol diacrylate (average number of addition moles of ethylene oxide: 9) to give a reaction mixture. Then, the reaction mixture was supplied to a reaction vessel formed by attaching a lid to a jacketed stainless double-arm kneader having two sigma-type blades and having an internal volume of 10 L. Nitrogen gas replacement of the system was conducted while keeping the reaction mixture at 30° C. Subsequently, to the reaction mixture were added 28.3 g of a 10% by weight aqueous solution of sodium persulfate and 1.5 g of a 1% by weight aqueous solution of L-ascorbic acid while stirring. Approximately one minute later, polymerization was initiated. In 15 minutes following initiation of the polymerization, a polymerization peak temperature of 86° C. was exhibited, and hydrous gelatinous polymer was recovered at 60 minutes after initiation of the polymerization. Thus resulting hydrous gelatinous polymer had been finely divided into particles of 1 to 4 mm, and the finely divided hydrous gelatinous polymer was spread over a wire mesh having a mesh opening size of 300 μm, followed by hot-air drying at 170° C. for 65 min. Then, the dried matter was pulverized using a roll mill, and further classified with a wire mesh having a mesh opening size of 850 μm and formulated. Accordingly, a water absorbing resin (1) having an irregular crushed shape was obtained.

Reference Example 2

Polymerization and drying were conducted similarly to Reference Example 1. Then, the dried matter was pulverized using a roll mill, and further classified with a wire mesh having a mesh opening size of 850 μm and formulated. Accordingly, a water absorbing resin (2) having an irregular crushed shape was obtained.

Reference Example 3

In 5500 g of an aqueous solution of sodium acrylate having a neutralization ratio of 68% by mole (monomer concentration: 38% by weight) was dissolved 5.02 g of polyethylene glycol diacrylate (average number of addition moles of ethylene oxide: 9) to give a reaction mixture. Then, the reaction mixture was supplied to a reaction vessel formed by attaching a lid to a jacketed stainless double-arm kneader having two sigma-type blades and having an internal volume of 10 L. Nitrogen gas replacement of the system was conducted while keeping the reaction mixture at 30° C. Subsequently, to the reaction mixture were added 28.8 g of a 10% by weight aqueous solution of sodium persulfate and 1.5 g of a 1% by weight aqueous solution of L-ascorbic acid while stirring. Approximately one minute later, polymerization was initiated. In 15 minutes following initiation of the polymerization, a polymerization peak temperature of 86° C. was exhibited, and hydrous gelatinous polymer was recovered at 60 minutes after initiation of the polymerization. Thus resulting hydrous gelatinous polymer had been finely divided into particles of 1 to 4 mm, and the finely divided hydrous gelatinous polymer was spread over a 50 mesh-sized wire mesh (mesh opening size: 300 μm), followed by hot-air drying at 170° C. for 65 min. Then, the dried matter was pulverized using a roll mill, and further classified with a wire mesh having a mesh opening size of 850 μm and formulated. Accordingly, a water absorbing resin (3) having an irregular crushed shape was obtained.

Reference Example 4

Polymerization and drying were conducted similarly to Reference Example 3. Then, the dried matter was pulverized using a roll mill, and further classified with a wire mesh having a mesh opening size of 850 μm and formulated. Accordingly, a water absorbing resin (4) having an irregular crushed shape was obtained.

Reference Example 5

In 5500 g of an aqueous solution of sodium acrylate having a neutralization ratio of 75% by mole (monomer concentration: 38% by weight) was dissolved 8.6 g of polyethylene glycol diacrylate (average number of addition moles of ethylene oxide: 9) to give a reaction mixture. Then, the reaction mixture was supplied to a reaction vessel formed by attaching a lid to a jacketed stainless double-arm kneader having two sigma-type blades and having an internal volume of 10 L. Nitrogen gas replacement of the system was conducted while keeping the reaction mixture at 30° C. Subsequently, to the reaction mixture were added 28.3 g of a 10% by weight aqueous solution of sodium persulfate and 1.5 g of a 1% by weight aqueous solution of L-ascorbic acid while stirring. Approximately one minute later, polymerization was initiated. In 15 minutes following initiation of the polymerization, a polymerization peak temperature of 90° C. was exhibited, and hydrous gelatinous polymer was recovered at 60 minutes after initiation of the polymerization. Thus resulting hydrous gelatinous polymer had been finely divided into particles of 1 to 4 mm, and the finely divided hydrous gelatinous polymer was spread over a 50 mesh-sized wire mesh (mesh opening size: 300 μm), followed by hot-air drying at 170° C. for 65 min. Then, the dried matter was pulverized using a roll mill, and further classified with a wire mesh having a mesh opening size of 850 μm and formulated. Accordingly, a water absorbing resin (5) having an irregular crushed shape was obtained.

Reference Example 6

Polymerization and drying were conducted similarly to Reference Example 5. Then, the dried matter was pulverized using a roll mill, and further classified with a wire mesh having a mesh opening size of 850 μm and formulated. Accordingly, a water absorbing resin (6) having an irregular crushed shape was obtained.

Example 1

With 100 parts by weight of the water absorbing resin (1) obtained in Reference Example 1 was mixed 3.93 parts by weight of a surface crosslinking agent containing 0.55 parts by weight of propylene glycol, 0.03 parts by weight of ethylene glycol diglycidyl ether, 0.35 parts by weight of 1,4-butanediol and 3 parts by weight of water. The mixture was subjected to a heat treatment at 210° C. for 45 min to obtain a water absorbing resin (1)-1. With 100 parts by weight of the water absorbing resin (1)-1 was further mixed by spraying 4 parts by weight of water. Thus resulting mixture was hardened at 60° C. for 1 hour to give a particulate water absorbing agent (1).

Example 2

A particulate water absorbing agent (2) was obtained in a similar manner to Example 1 except that the water absorbing resin (1) obtained in Reference Example 1 was changed to the water absorbing resin (2) obtained in Reference Example 2.

Example 3

A particulate water absorbing agent (3) was obtained in a similar manner to Example 1 except that the water absorbing resin (1) obtained in Reference Example 1 was changed to the water absorbing resin (3) obtained in Reference Example 3.

Example 4

A particulate water absorbing agent (4) was obtained in a similar manner to Example 1 except that the water absorbing resin (1) obtained in Reference Example 1 was changed to the water absorbing resin (4) obtained in Reference Example 4.

Example 5

A particulate water absorbing agent (5) was obtained in a similar manner to Example 1 except that the water absorbing resin (1) obtained in Reference Example 1 was changed to the water absorbing resin (5) obtained in Reference Example 5.

Example 6

A particulate water absorbing agent (6) was obtained in a similar manner to Example 1 except that the water absorbing resin (1) obtained in Reference Example 1 was changed to the water absorbing resin (6) obtained in Reference Example 6.

Example 7

With 100 parts by weight of the water absorbing resin (1) obtained in Reference Example 1 was mixed 4.0 parts by weight of a surface crosslinking agent containing 0.55 parts by weight of propylene glycol, 0.1 parts by weight of ethylene carbonate, 0.35 parts by weight of 1,4-butanediol and 3 parts by weight of water. The mixture was subjected to a heat treatment at 210° C. for 45 min to obtain a water absorbing resin (7)-1. With 100 parts by weight of the water absorbing resin (7)-1 was further mixed by spraying 4 parts by weight of water. Thus resulting mixture was hardened at 60° C. for 1 hour to give a particulate water absorbing agent (7).

Example 8

With 100 parts by weight of the water absorbing resin (1) obtained in Reference Example 1 was mixed 4.03 parts by weight of a surface crosslinking agent containing 0.55 parts by weight of propylene glycol, 0.03 parts by weight of ethylene glycol diglycidyl ether, 0.1 parts by weight of ethylene carbonate, 0.35 parts by weight of 1,4-butanediol and 3 parts by weight of water. The mixture was subjected to a heat treatment at 210° C. for 40 min to obtain a water absorbing resin (8)-1. With 100 parts by weight of the water absorbing resin (8)-1 was further mixed by spraying 4 parts by weight of water. Thus resulting mixture was hardened at 60° C. for 1 hour to give a particulate water absorbing agent (8).

Example 9

With 100 parts by weight of the water absorbing resin (1) obtained in Reference Example 1 was mixed 3.93 parts by weight of a surface crosslinking agent containing 0.55 parts by weight of propylene glycol, 0.03 parts by weight of ethylene glycol diglycidyl ether, 0.35 parts by weight of 1,4-butanediol and 3 parts by weight of water. The mixture was subjected to a heat treatment at 210° C. for 45 min to obtain a water absorbing resin (9)-1. With 100 parts by weight of the water absorbing resin (9)-1 were further mixed by spraying 4 parts by weight of water, 0.5 parts by weight of a 15% by weight aqueous solution of leaf extract of the aqueous plant as a plant component (A1). Thus resulting mixture was hardened at 60° C. for 1 hour to give a particulate water absorbing agent (9). Product name of this 15% by weight aqueous solution of leaf extract of the aqueous plant was FS-80MO, supplied by SHIRAIMATSU PHARMACEUTICAL Co., LTD (address: Shiga-ken Kouga-gun, Minakuchi-cho Ukawa 37-1)).

Reference Example 7

A water absorbing resin (7) having an irregular crushed shape was obtained in a similar manner to Reference Example 1 except that formulation conditions were changed.

Example 10

A particulate water absorbing agent (10) was obtained in a similar manner to Example 1 except that weight of water mixed by spraying was changed to give 8 parts by weight.

Example 11

Evaluation of the conveying speed of the particulate water absorbing agent (1) obtained in Example 1 was made.

Comparative Example 1

A particulate water absorbing agent for comparison (1) was obtained in a similar manner to Example 1 except that mixing by spraying of water was not conducted.

Comparative Example 2

With 100 parts by weight of the water absorbing resin (1) obtained in Reference Example 1 was mixed 3.9 parts by weight of a surface crosslinking agent containing 0.55 parts by weight of propylene glycol, 0.35 parts by weight of 1,4-butanediol and 3 parts by weight of water. The mixture was subjected to a heat treatment at 210° C. for 45 min to obtain a water absorbing resin for comparison (2)-1. With 100 parts by weight of the water absorbing resin for comparison (2)-1 was further mixed by spraying 4 parts by weight of water. Thus resulting mixture was hardened at 60° C. for 1 hour to give a particulate water absorbing agent for comparison (2).

Comparative Example 3

With 100 parts by weight of the water absorbing resin (1) obtained in Reference Example 1 was mixed 3.93 parts by weight of a surface crosslinking agent containing 0.55 parts by weight of propylene glycol, 0.03 parts by weight of ethylene glycol diglycidyl ether, 0.35 parts by weight of 1,4-butanediol and 3 parts by weight of water. The mixture was subjected to a heat treatment at 210° C. for 25 min to obtain a water absorbing resin for comparison (3)-1. With 100 parts by weight of the water absorbing resin for comparison (3)-1 was further mixed by spraying 4 parts by weight of water. Thus resulting mixture was hardened at 60° C. for 1 hour to give a particulate water absorbing agent for comparison (3).

Comparative Example 4

A particulate water absorbing agent for comparison (4) was obtained in a similar manner to Example 1 except that time period of the heat treatment was changed to 70 min.

Comparative Example 5

A particulate water absorbing agent for comparison (5) was obtained in a similar manner to Example 1 except that the water absorbing resin (1) obtained in Reference Example 1 was changed to the water absorbing resin (7) obtained in Reference Example 7.

Comparative Example 6

With 100 parts by weight of the water absorbing resin (1) obtained in Reference Example 1 was mixed 7.4 parts by weight of a surface crosslinking agent containing 2.0 parts by weight of propylene glycol, 0.4 parts by weight of 2-oxazolidinone and 5 parts by weight of water to give a mixture. This mixture was subjected to a heat treatment at 185° C. for 70 min to obtain a water absorbing resin for comparison (6)-1. With 100 parts by weight of the water absorbing resin for comparison (6)-1 was mixed by spraying 4 parts by weight of water. A particulate water absorbing agent for comparison (6) was obtained by drying to harden thus resulting mixture at 60° C. for 1 hour.

Comparative Example 7

Evaluation of the conveying speed of the particulate water absorbing agent for comparison (1) obtained in Comparative Example 1 was made.

Example 12

In order to evaluate the particulate water absorbing agent (1) obtained in Example 1 on performances as an absorbent core, an absorbent core for evaluation (1) was produced according to the above method for (h) Evaluation of Absorbent Core Performance.

Example 13

In order to evaluate the particulate water absorbing agent (5) obtained in Example 5 on performances as an absorbent core, an absorbent core for evaluation (2) was produced according to the above method for (h) Evaluation of Absorbent Core Performance.

Comparative Example 8

In order to evaluate the particulate water absorbing agent for comparison (2) obtained in Comparative Example 2 on performances as an absorbent core, an absorbent core for comparison evaluation (1) was produced according to the above method for (h) Evaluation of Absorbent Core Performance.

Comparative Example 9

In order to evaluate the particulate water absorbing agent for comparison (3) obtained in Comparative Example 3 on performances as an absorbent core, an absorbent core for comparison evaluation (2) was produced according to the above method for (h) Evaluation of Absorbent Core Performance.

Comparative Example 10

In order to evaluate the particulate water absorbing agent for comparison (4) obtained in Comparative Example 4 on performances as an absorbent core, an absorbent core for comparison evaluation (3) was produced according to the above method for (h) Evaluation of Absorbent Core Performance.

Comparative Example 11

In order to evaluate the particulate water absorbing agent for comparison (5) obtained in Comparative Example 5 on performances as an absorbent core, an absorbent core for comparison evaluation (4) was produced according to the above method for (h) Evaluation of Absorbent Core Performance.

Example 14

Using the particulate water absorbing agent (1) obtained in Example 1, 100 pieces of absorbent core were continuously produced with an absorbent core maker. From the 100 pieces of the produced absorbent core were picked up 10 pieces at random, and the amount of the particulate water absorbing agent (1) in the absorbent core was measured. Measurement results and standard deviation are shown in Table 6.

Comparative Example 12

Using the particulate water absorbing agent for comparison (1) obtained in Comparative Example 1, 100 pieces of absorbent core were continuously produced with an absorbent core maker. From the 100 pieces of the produced absorbent core were picked up 10 pieces at random, and the amount of the particulate water absorbing agent for comparison (1) in the absorbent core was measured. The absorbent core maker and settings thereof are exactly the same as those in Example 14. Measurement results and standard deviation are shown in Table 6.

The water absorbing resins (1) to (7) obtained in the above Reference Examples were analyzed, and their CRC, particle size distribution, mass median particle size (D50) and logarithmic standard deviation are shown in Table 1.

The particulate water absorbing agents (1) to (10) and particulate water absorbing agents for comparison (1) to (6) obtained in the above Examples and Comparative Examples were analyzed, and their CRC, AAP: 0.9 g, PPUP, frictional charge and moisture content are shown in Table 2.

The particulate water absorbing agents (1) to (10) and particulate water absorbing agents for comparison (1) to (6) obtained in the above Examples and Comparative Examples were analyzed, and their particle size distribution, mass median particle size (D50) and logarithmic standard deviation are shown in Table 3.

Results demonstrating the data of the conveying speed, standard deviation, conveying speed stability index of the particulate water absorbing agent (1) obtained in the above Example 1 and of the particulate water absorbing agent for comparison (1) obtained in the above Comparative Example (1) are shown in Table 4.

Rewet amount on the absorbent core for evaluation (1) obtained in the above Example 12, the absorbent core for evaluation (2) obtained in the above Example 13, and the absorbent cores for comparison for evaluation (1) to (4) obtained in the above Comparative Examples (8) to (11) was measured. Their measurement results are shown in Table 5.

TABLE 1

Specifications and Evaluation results of Reference Examples

| Reference Example | Water absorbing resin | Centrifuge retention capacity (g/g) | 850 μm or greater (% by weight) | 710 μm or greater and less than 850 μm (% by weight) | 600 μm or greater and less than 710 μm (% by weight) | 500 μm or greater and less than 600 μm (% by weight) | 425 μm or greater and less than 500 μm (% by weight) | 300 μm or greater and less than 425 μm (% by weight) |
|---|---|---|---|---|---|---|---|---|
| Reference Example 1 | Water absorbing resin (1) | 46 | 0.0 | 0.7 | 3.5 | 8.9 | 15.9 | 36.1 |
| Reference Example 2 | Water absorbing resin (2) | 46 | 0.0 | 1.6 | 18.4 | 21.5 | 18.3 | 25.2 |
| Reference Example 3 | Water absorbing resin (3) | 44 | 0.0 | 1.9 | 21.1 | 19.6 | 16.5 | 23.9 |
| Reference Example 4 | Water absorbing resin (4) | 44 | 0.0 | 0.7 | 3.5 | 9.9 | 17.3 | 37.3 |
| Reference Example 5 | Water absorbing resin (5) | 39 | 0.0 | 1.9 | 21.1 | 18.4 | 15.8 | 23.8 |
| Reference Example 6 | Water absorbing resin (6) | 39 | 0.0 | 0.7 | 3.5 | 9.9 | 17.3 | 37.3 |
| Reference Example 7 | Water absorbing resin (7) | 44 | 0.0 | 0.0 | 0.0 | 0.0 | 0.4 | 10.1 |

| Reference Example | Water absorbing resin | 212 μm or greater and less than 300 μm (% by weight) | 150 μm or greater and less than 212 μm (% by weight) | 45 μm or greater and less than 150 μm (% by weight) | less than 45 μm (% by weight) | D50 | σζ |
|---|---|---|---|---|---|---|---|
| Reference Example 1 | Water absorbing resin (1) | 20.9 | 8.8 | 5.0 | 0.2 | 346 | 0.39 |

TABLE 1-continued

Specifications and Evaluation results of Reference Examples

| | | | | | | | | |
|---|---|---|---|---|---|---|---|---|
| Reference Example 2 | Water absorbing resin (2) | 11.0 | 3.0 | 0.9 | 0.1 | 464 | 0.35 |
| Reference Example 3 | Water absorbing resin (3) | 11.1 | 3.9 | 1.9 | 0.1 | 465 | 0.38 |
| Reference Example 4 | Water absorbing resin (4) | 18.1 | 8.0 | 5.0 | 0.2 | 357 | 0.39 |
| Reference Example 5 | Water absorbing resin (5) | 12.7 | 4.3 | 1.9 | 0.1 | 458 | 0.40 |
| Reference Example 6 | Water absorbing resin (6) | 18.1 | 8.0 | 5.0 | 0.2 | 357 | 0.39 |
| Reference Example 7 | Water absorbing resin (7) | 29.5 | 28.9 | 30.1 | 1.0 | 188 | 0.47 |

TABLE 2

Specifications and Evaluation results of Examples and Comparative Examples

| | Particulate water absorbing agent | Centrifuge retention capacity (g/g) | Absorbency against pressure (AAP: 0.90 g) (g/g) | Permeability potential under pressure at 4.9 kPa (%) | Frictional charge | Moisture content (%) |
|---|---|---|---|---|---|---|
| Example 1 | Particulate water absorbing agent (1) | 32 | 21 | 68 | + (Positive charge) | 2.5 |
| Example 2 | Particulate water absorbing agent (2) | 33 | 21 | 70 | + (Positive charge) | 2.3 |
| Example 3 | Particulate water absorbing agent (3) | 29 | 20 | 81 | + (Positive charge) | 2.4 |
| Example 4 | Particulate water absorbing agent (4) | 29 | 21 | 72 | + (Positive charge) | 2.5 |
| Example 5 | Particulate water absorbing agent (5) | 29 | 24 | 75 | + (Positive charge) | 2.3 |
| Example 6 | Particulate water absorbing agent (6) | 30 | 23 | 70 | + (Positive charge) | 3.5 |
| Example 7 | Particulate water absorbing agent (7) | 32 | 21 | 65 | + (Positive charge) | 3.0 |
| Example 8 | Particulate water absorbing agent (8) | 34 | 22 | 70 | + (Positive charge) | 2.4 |
| Example 9 | Particulate water absorbing agent (9) | 32 | 21 | 68 | + (Positive charge) | 2.6 |
| Example 10 | Particulate water absorbing agent (10) | 31 | 21 | 65 | + (Positive charge) | 5.6 |
| Comparative Example 1 | Particulate water absorbing agent for comparison (1) | 32 | 21 | 68 | + (Positive charge) | 0.2 |
| Comparative Example 2 | Particulate water absorbing agent for comparison (2) | 32 | 19 | 45 | − (Negative charge) | 2.5 |
| Comparative Example 3 | Particulate water absorbing agent for comparison (3) | 35 | 20 | 25 | + (Positive charge) | 2.6 |
| Comparative Example 4 | Particulate water absorbing agent for comparison (4) | 26 | 21 | 75 | + (Positive charge) | 2.7 |
| Comparative Example 5 | Particulate water absorbing agent for comparison (5) | 29 | 19 | 35 | + (Positive charge) | 2.5 |
| Comparative Example 6 | Particulate water absorbing agent for comparison (6) | 33 | 21 | 35 | − (Negative charge) | 2.6 |

TABLE 3

Specifications and Evaluation results of Examples and Comparative Examples

| | Particulate water absorbing agent | 850 μm or greater (% by weight) | 710 μm or greater and less than 850 μm (% by weight) | 600 μm or greater and less than 710 μm (% by weight) | 500 μm or greater and less than 600 μm (% by weight) | 425 μm or greater and less than 500 μm (% by weight) | 300 μm or greater and less than 425 μm (% by weight) |
|---|---|---|---|---|---|---|---|
| Example 1 | Particulate water absorbing agent (1) | 0.0 | 0.8 | 4.0 | 9.1 | 16.5 | 35.1 |
| Example 2 | Particulate water absorbing agent (2) | 0.0 | 1.5 | 19.0 | 22.2 | 19.7 | 24.0 |
| Example 3 | Particulate water absorbing agent (3) | 0.0 | 1.9 | 22.0 | 23.2 | 17.0 | 22.1 |
| Example 4 | Particulate water absorbing agent (4) | 0.0 | 0.7 | 4.2 | 10.1 | 19.0 | 34.9 |
| Example 5 | Particulate water absorbing agent (5) | 0.0 | 1.6 | 20.8 | 19.0 | 16.0 | 23.8 |
| Example 6 | Particulate water absorbing agent (6) | 0.0 | 0.6 | 3.0 | 11.1 | 17.3 | 37.3 |

TABLE 3-continued

Specifications and Evaluation results of Examples and Comparative Examples

| | | | | | | | |
|---|---|---|---|---|---|---|---|
| Example 7 | Particulate water absorbing agent (7) | 0.0 | 0.5 | 3.0 | 6.5 | 20.1 | 35.1 |
| Example 8 | Particulate water absorbing agent (8) | 0.0 | 0.4 | 2.5 | 7.0 | 22.5 | 32.8 |
| Example 9 | Particulate water absorbing agent (9) | 0.0 | 0.7 | 4.1 | 7.2 | 21.0 | 33.1 |
| Example 10 | Particulate water absorbing agent (10) | 0.0 | 1.5 | 5.0 | 12.0 | 19.0 | 34.3 |
| Comparative Example 1 | Particulate water absorbing agent for comparison (1) | 0.0 | 0.7 | 3.5 | 8.9 | 16.5 | 36.1 |
| Comparative Example 2 | Particulate water absorbing agent for comparison (2) | 0.0 | 0.6 | 3.0 | 9.4 | 15.9 | 36.1 |
| Comparative Example 3 | Particulate water absorbing agent for comparison (3) | 0.0 | 0.7 | 3.5 | 8.9 | 18.0 | 36.2 |
| Comparative Example 4 | Particulate water absorbing agent for comparison (4) | 0.0 | 1.2 | 4.1 | 10.0 | 16.9 | 35.1 |
| Comparative Example 5 | Particulate water absorbing agent for comparison (5) | 0.0 | 0.0 | 0.0 | 0.0 | 0.4 | 14.5 |
| Comparative Example 6 | Particulate water absorbing agent for comparison (6) | 0.0 | 2.1 | 5.3 | 10.5 | 18.4 | 33.2 |

| | Particulate water absorbing agent | 212 μm or greater and less than 300 μm (% by weight) | 150 μm or greater and less than 212 μm (% by weight) | 45 μm or greater and less than 150 μm (% by weight) | less than 45 μm (% by weight) | D50 | σζ |
|---|---|---|---|---|---|---|---|
| Example 1 | Particulate water absorbing agent (1) | 22.9 | 7.8 | 3.7 | 0.1 | 349 | 0.37 |
| Example 2 | Particulate water absorbing agent (2) | 10.1 | 2.8 | 0.7 | 0.0 | 471 | 0.34 |
| Example 3 | Particulate water absorbing agent (3) | 10.3 | 2.8 | 0.7 | 0.0 | 487 | 0.34 |
| Example 4 | Particulate water absorbing agent (4) | 21.0 | 7.0 | 3.0 | 0.1 | 363 | 0.36 |
| Example 5 | Particulate water absorbing agent (5) | 15.2 | 2.7 | 0.9 | 0.0 | 458 | 0.38 |
| Example 6 | Particulate water absorbing agent (6) | 19.0 | 8.2 | 3.4 | 0.1 | 360 | 0.37 |
| Example 7 | Particulate water absorbing agent (7) | 23.2 | 8.6 | 3.0 | 0.0 | 348 | 0.36 |
| Example 8 | Particulate water absorbing agent (8) | 23.8 | 8.6 | 2.4 | 0.0 | 352 | 0.35 |
| Example 9 | Particulate water absorbing agent (9) | 22.4 | 8.7 | 2.8 | 0.0 | 355 | 0.37 |
| Example 10 | Particulate water absorbing agent (10) | 20.1 | 5.6 | 2.5 | 0.0 | 375 | 0.36 |
| Comparative Example 1 | Particulate water absorbing agent for comparison (1) | 21.4 | 8.8 | 4.0 | 0.1 | 348 | 0.38 |
| Comparative Example 2 | Particulate water absorbing agent for comparison (2) | 22.0 | 8.8 | 4.1 | 0.1 | 346 | 0.38 |
| Comparative Example 3 | Particulate water absorbing agent for comparison (3) | 22.8 | 6.8 | 3.1 | 0.0 | 354 | 0.35 |
| Comparative Example 4 | Particulate water absorbing agent for comparison (4) | 20.4 | 7.9 | 4.3 | 0.1 | 356 | 0.39 |
| Comparative Example 5 | Particulate water absorbing agent for comparison (5) | 29.5 | 26.3 | 28.6 | 0.7 | 198 | 0.48 |
| Comparative Example 6 | Particulate water absorbing agent for comparison (6) | 19.4 | 7.6 | 3.5 | 0.0 | 369 | 0.39 |

TABLE 4

Evaluation results of Examples and Comparative Examples

| Conveying time (sec) | Example 11 Particulate water absorbing agent (1) Conveying speed (g/sec) | Comparative Example 7 Particulate water absorbing agent for comparison (1) Conveying speed (g/sec) |
|---|---|---|
| 30 | 11.3 | 10.1 |
| 60 | 11.7 | 10.7 |
| 90 | 11.8 | 11.1 |
| 120 | 11.6 | 11.2 |
| 150 | 11.7 | 11.4 |
| 180 | 11.6 | 11.4 |
| 210 | 11.7 | 11.6 |
| 240 | 11.8 | 11.5 |
| 270 | 11.7 | 11.8 |
| 300 | 11.8 | 11.6 |
| Average conveying speed: Fave. (g/s) | 11.7 | 11.2 |
| Standard deviation of conveying speed | 0.15 | 0.50 |
| Conveying speed stability index: FI(%) | 1.31% | 4.5% |

TABLE 5

Evaluation results of Examples and Comparative Examples

| | | Rewet amount (g) |
|---|---|---|
| Example 12 | Absorbent core for evaluation (1) | 5 |
| Example 13 | Absorbent core for evaluation (2) | 3 |
| Comparative Example 8 | Absorbent core for comparison for evaluation (1) | 10 |
| Comparative Example 9 | Absorbent core for comparison for evaluation (2) | 10 |
| Comparative Example 10 | Absorbent core for comparison for evaluation (3) | 14 |
| Comparative Example 11 | Absorbent core for comparison for evaluation (4) | 11 |

TABLE 6

Evaluation results of Examples and Comparative Examples

| Evaluation sample | Example 14 Amount of particulate water absorbing agent (1) (g) | Comparative Example 12 Amount of particulate water absorbing agent for comparison (1) (g) |
|---|---|---|
| 1 | 13 | 12 |
| 2 | 13 | 14 |
| 3 | 14 | 13 |
| 4 | 14 | 14 |
| 5 | 13 | 12 |
| 6 | 13 | 13 |
| 7 | 13 | 14 |
| 8 | 14 | 14 |
| 9 | 13 | 13 |
| 10 | 13 | 12 |
| Mean value of amount of particulate water absorbing agent in absorbent core (g) | 13 | 13 |
| Standard deviation of amount of particulate water absorbing agent in absorbent core | 0.48 | 0.94 |

As shown in Table 2, the particulate water absorbing agents of the present invention exhibit high centrifuge retention capacity, absorbency against pressure as well as permeability potential under pressure, and are extremely excellent in absorption performance.

These particulate water absorbing agents of the present invention are also excellent in powder flowability, and as shown in Table 4, they exhibit high conveying speed stability index.

Because the particulate water absorbing agent of the present invention provides an absorbent core accompanied by a small rewet amount as shown in Table 5, absorbing articles (diapers) with stable and high performances can be provided without evoking unpleasantness to the user.

As shown in Table 4, the particulate water absorbing agent of the present invention exhibits high conveying speed stability index. Therefore, also in cases in which absorbent cores are continuously produced in effect, less variance of amount of the particulate water absorbing agent in the absorbent core is achieved as shown in Table 6. Accordingly, production of absorbent cores with stable performances is enabled.

INDUSTRIAL APPLICABILITY

The particulate water absorbing agent obtained according to the present invention is excellent in powder conveying property and absorption performance, therefore, when it is used in absorbent cores such as diapers, absorbent cores having very excellent absorption performance and feel in use can be provided.

The invention claimed is:

1. A particulate water absorbing agent comprising: (A) a water-swelling crosslinked polymer having a constitutional unit derived from an unsaturated monomer containing an acid group and/or a salt thereof; and (B) water, said particulate water absorbing agent having:
    (a) centrifuge retention capacity (CRC) for a 0.90% by weight aqueous sodium chloride solution being 28 to 50 g/g;
    (b) absorbency against pressure (AAP: 0.90 g) being 20 to 40 g/g;
    (c) moisture content determined on the basis of the weight loss in drying at 105° C. for 3 hrs being 2 to 10% by weight;
    (d) positive frictional charge when the moisture content determined on the basis of the weight loss in drying at 105° C. for 3 hrs is not higher than 0.5% by weight; and
    (e) permeability potential under pressure (PPUP) being 60 to 100% specified by the following formula (I):

$$PPUP(\%) = (AAP: 5.0\ g)/(AAP: 0.90\ g) * 100 \quad (I)$$

wherein (AAP: 0.90 g) is the absorbency against pressure measured with 0.90 g of the particulate water absorbing agent for a 0.90% by weight aqueous sodium chloride solution under a pressure of 4.8 kPa for 60 min; and (AAP: 5.0 g) is the absorbency against pressure measured with 5.0 g of the particulate water absorbing agent for a 0.90% by weight aqueous sodium chloride solution under a pressure of 4.8 kPa for 60 min.

2. The particulate water absorbing agent according to claim 1 wherein the conveying speed stability index is 0 to 4.0%.

3. The particulate water absorbing agent according to claim 1 wherein the weight average particle diameter as specified by standard sieve classification is 200 to 500 μm, and particles being not smaller than 150 μm account for 90 to 100% by weight of the total.

4. The particulate water absorbing agent according to claim 1 which further comprises a plant component (A1).

5. An absorbent core for sanitary goods formed to comprise the particulate water absorbing agent according to claim 1, and a hydrophilic fiber having a negative frictional charge.

6. An absorbing article which comprises the absorbent core according to claim 5, a front face sheet having liquid permeability, and a back face sheet having liquid impermeability.

7. The particulate water absorbing agent according to claim 1, wherein said water-swelling crosslinked polymer is surface crosslinked with a surface crosslinking agent to provide a positive frictional charge.

* * * * *